(12) United States Patent
Segal et al.

(10) Patent No.: US 7,538,400 B2
(45) Date of Patent: May 26, 2009

(54) SENSOR PLATFORM USING A NON-HORIZONTALLY ORIENTED NANOTUBE ELEMENT

(75) Inventors: Brent M. Segal, Woburn, MA (US); Thomas Rueckes, Rockport, MA (US); Bernhard Vogeli, Zurich (CH); Darren K. Brock, Woburn, MA (US); Venkatachalam C. Jaiprakash, Fremont, CA (US); Claude L. Bertin, South Burlington, VT (US)

(73) Assignee: Nantero, Inc., Woburn, MA (US)

( * ) Notice: Subject to any disclaimer, the term of this patent is extended or adjusted under 35 U.S.C. 154(b) by 572 days.

(21) Appl. No.: 11/333,623

(22) Filed: Jan. 17, 2006

(65) Prior Publication Data
US 2006/0125033 A1   Jun. 15, 2006

Related U.S. Application Data

(63) Continuation of application No. 10/844,883, filed on May 12, 2004, now Pat. No. 7,385,266.

(60) Provisional application No. 60/470,410, filed on May 14, 2003, provisional application No. 60/470,371, filed on May 14, 2003, provisional application No. 60/501,143, filed on Sep. 8, 2003.

(51) Int. Cl.
*H01L 49/00* (2006.01)
*G01N 27/02* (2006.01)

(52) U.S. Cl. .............. 257/414; 73/31.06; 977/904; 977/920

(58) Field of Classification Search ............. 257/414; 73/31.06; 977/904, 920
See application file for complete search history.

(56) References Cited

U.S. PATENT DOCUMENTS
6,057,637 A   5/2000   Zettl et al.

(Continued)

FOREIGN PATENT DOCUMENTS
EP   1 061 040 A1   12/2000

(Continued)

OTHER PUBLICATIONS
U.S. Appl. No. 10/341,005, filed Jan. 13, 2003, Ward.

(Continued)

*Primary Examiner*—Evan Pert
(74) *Attorney, Agent, or Firm*—Wilmer Cutler Pickering Hale and Dorr LLP

(57) ABSTRACT

Sensor platforms and methods of making them are described. A platform having a non-horizontally oriented sensor element comprising one or more nanostructures such as nanotubes is described. Under certain embodiments, a sensor element has or is made to have an affinity for an analyte. Under certain embodiments, such a sensor element comprises one or more pristine nanotubes. Under certain embodiments, the sensor element comprises derivatized or functionalized nanotubes. Under certain embodiments, a sensor is made by providing a support structure; providing one or more nanotubes on the structure to provide material for a sensor element; and providing circuitry to electrically sense the sensor element's electrical characterization. Under certain embodiments, the sensor element comprises pre-derivatized or pre-functionalized nanotubes. Under other embodiments, sensor material is derivatized or functionalized after provision on the structure or after patterning. Under certain embodiments, a large-scale array of sensor platforms includes a plurality of sensor elements.

7 Claims, 22 Drawing Sheets

U.S. PATENT DOCUMENTS

| | | |
|---|---|---|
| 6,187,823 B1 | 2/2001 | Haddon et al. |
| 6,277,318 B1 | 8/2001 | Bower et al. |
| 6,331,262 B1 | 12/2001 | Haddon et al. |
| 6,342,276 B1 | 1/2002 | You |
| 6,368,569 B1 | 4/2002 | Haddon et al. |
| 6,409,567 B1 | 6/2002 | Amey, Jr. et al. |
| 6,423,583 B1 | 7/2002 | Avouris et al. |
| 6,495,116 B1 | 12/2002 | Herman |
| 6,495,258 B1 | 12/2002 | Chen et al. |
| 6,515,339 B2 | 2/2003 | Shin et al. |
| 6,528,020 B1 | 3/2003 | Dai et al. |
| 6,531,513 B2 | 3/2003 | Haddon et al. |
| 6,630,772 B1 | 10/2003 | Bower et al. |
| 6,641,793 B2 | 11/2003 | Haddon et al. |
| 6,645,628 B2 | 11/2003 | Shiffler, Jr. et al. |
| 6,706,402 B2 | 3/2004 | Rueckes et al. |
| 6,707,098 B2 | 3/2004 | Hofmann et al. |
| 6,752,977 B2 | 6/2004 | Smalley et al. |
| 6,808,746 B1 | 10/2004 | Dai et al. |
| 6,833,558 B2 | 12/2004 | Lee et al. |
| 6,858,197 B1 | 2/2005 | Delzeit |
| 6,863,942 B2 | 3/2005 | Ren et al. |
| 6,894,359 B2 | 5/2005 | Bradley et al. |
| 6,896,864 B2 | 5/2005 | Clarke |
| 6,899,945 B2 | 5/2005 | Smalley et al. |
| 6,918,284 B2 | 7/2005 | Snow et al. |
| 6,919,592 B2 | 7/2005 | Segal et al. |
| 6,919,740 B2 | 7/2005 | Snider |
| 6,921,575 B2 | 7/2005 | Horiuchi et al. |
| 6,924,538 B2 | 8/2005 | Jaiprakash et al. |
| 6,946,410 B2 | 9/2005 | French et al. |
| 7,048,999 B2 | 5/2006 | Smalley et al. |
| 7,057,402 B2 | 6/2006 | Cole et al. |
| 7,115,864 B2 | 10/2006 | Colbert et al. |
| 2001/0004979 A1 | 6/2001 | Han et al. |
| 2002/0081380 A1 | 6/2002 | Dillon et al. |
| 2002/0160111 A1 | 10/2002 | Sun et al. |
| 2003/0004058 A1 | 1/2003 | Li et al. |
| 2003/0065206 A1 | 4/2003 | Bolskar et al. |
| 2003/0122111 A1 | 7/2003 | Glatkowski |
| 2003/0177450 A1 | 9/2003 | Nugent |
| 2003/0200521 A1 | 10/2003 | DeHon et al. |
| 2003/0220518 A1 | 11/2003 | Bolskar et al. |
| 2004/0005723 A1 | 1/2004 | Empedocles et al. |
| 2004/0007528 A1 | 1/2004 | Bakajin et al. |
| 2004/0023253 A1 | 2/2004 | Kunwar et al. |
| 2004/0023514 A1 | 2/2004 | Moriya et al. |
| 2004/0034177 A1 | 2/2004 | Chen |
| 2004/0041154 A1 | 3/2004 | Watanabe et al. |
| 2004/0043527 A1 | 3/2004 | Bradley et al. |
| 2004/0071949 A1 | 4/2004 | Glatkowski et al. |
| 2004/0099438 A1 | 5/2004 | Arthur et al. |
| 2004/0104129 A1 | 6/2004 | Gu et al. |
| 2004/0181630 A1 | 9/2004 | Jaiprakash et al. |
| 2004/0253167 A1 | 12/2004 | Silva et al. |
| 2004/0265550 A1 | 12/2004 | Glatkowski et al. |
| 2005/0053525 A1 | 3/2005 | Segal et al. |
| 2005/0058797 A1 | 3/2005 | Sen et al. |
| 2005/0065741 A1 | 3/2005 | Segal et al. |
| 2005/0095938 A1 | 5/2005 | Rosenberger et al. |
| 2005/0269554 A1 | 12/2005 | Sen et al. |
| 2006/0052509 A1 | 3/2006 | Saitoh |
| 2006/0204427 A1 | 9/2006 | Ghenciu et al. |
| 2006/0237537 A1 | 10/2006 | Empedocles et al. |
| 2007/0004191 A1 | 1/2007 | Gu et al. |

FOREIGN PATENT DOCUMENTS

| | | |
|---|---|---|
| GB | 2 364 933 | 2/2002 |
| JP | 2000203821 | 7/2000 |
| JP | 2001 035362 | 9/2001 |
| JP | 2004090208 | 3/2004 |
| WO | WO-98/39250 A1 | 9/1998 |
| WO | WO-99/65821 A1 | 12/1999 |
| WO | WO-00/17101 | 3/2000 |
| WO | WO-2001/03208 | 1/2001 |
| WO | WO-2002/45113 | 1/2001 |
| WO | WO-02/48701 A2 | 6/2002 |
| WO | WO-02/060812 A2 | 8/2002 |
| WO | WO-03/016901 A1 | 2/2003 |
| WO | WO-03/022733 A2 | 3/2003 |
| WO | WO-03/034142 A1 | 4/2003 |
| WO | WO-2004/039893 | 10/2003 |
| WO | WO-03/019748 | 11/2003 |
| WO | WO-2004/065655 A1 | 8/2004 |
| WO | WO-2004/065657 | 8/2004 |
| WO | WO-2004/065671 | 8/2004 |
| WO | WO-2006/078293 A2 | 7/2006 |

OTHER PUBLICATIONS

Ajayan, P. M. et al., "Applications of Carbon Nanotubes", Appl. Phys., vol. 80, pp. 391-425, 2001.

Ausman, K. D. et al., "Organic Solvent Dispersement of Singlle-Walled Carbon Nanotubes: Toward Solutions of Pristine Nanotubes", The Journal of Physical Chemistry, vol. 104, No. 38, pp. 8911-8915, Sep. 28, 2000.

Bahr, J. L. et al., "Dissolution of small diamter single-wall carbon nanotubes in organic solvents", Chem. Commun., pp. 193-194, 2001.

Banerjee, S., "Functionalization of of Carbon Nanotubes with a Metal-Containing Molecular Complex", Nano Lett., 2002, vol. 2(1), pp. 49-53.

Berhan, L. et al., "Mechanical properties of nanotube sheets: Alterations in joint morphology and achievable moduli in manufacturable materials", Journal of Applied Physics, vol. 95, No. 8, pp. 4335-4345, Apr. 15, 2004.

Bonard, J. M. et al., "Monodisperse Multiwall Carbon Nanotubes Obtained with Ferritin as Catalyst", Nano Letters, vol. 2, No. 6, pp. 665-667, 2002.

Shelimov, Konstantic B. et al., "Pruification of Single-Wall Carbon Nanotubes by Ultrasonically Assisted Filtration," Chemical Physics Letters 282, Jan. 23, 1998, pp. 429-434.

Cassell, A. M. et al., "Large Scale CVD Synthesis of Single-Walled CarbonNanotubes", J. Phys. Chem. B., vol. 103, pp. 6484-6492, 1999.

Chen, B. et al., "Hetrogeneous Single-Walled Carbon Nanotube Catalyst Discovery and Optimization", Chem. Mater., vol. 14, pp. 1891-1896, 2002.

Chen, J. et al., "Dissolution of Full-Length Single-Walled Carbon Nanotubes" J. Phys. Chem. B., vol. 105, pp. 2525-2528, 2001.

Chen, J. et al., "Solution Properties of Single-Walled Carbon Nanotubes", Science, vol. 282, pp. 95-97, Oct. 2, 1998.

Chen, R.J. et al., "Nonconvalent Sidewall Functionalization of Single Walled Carbon Nanotubes for Protein Immobilization," J. Am.chem. Soc., 2001, vol. 123, pp. 3838-3839.

Cheng, H.M., "Large-scale and low-cost synthesis of single-walled carbon nanotubes by the catalytic pyrolysis of hydrocarbons", Applied Physica Letters, vol. 72, No. 25, pp. 3282-3284, Jun. 22, 1998.

Chiang, I.W. et al., "Purification and Characterization of Single-Wall Carbon Nanotubes (SWNTs) obtained from the Gas-Phase Decomposition of CO (HiPco Process )", J. Phys. Chem. B., vol. 105, pp. 8297-8301, 2001.

Colomer, J. F. et al., "Different purification methods of carbon nanotubes produced by catalytic synthesis", Synthetic Metals, vol. 103, pp. 2482-2483, 1999.

Dai, H. et al., "Controlled Chemical Routes to Nanotube Architectures, Physics, and Devices", J. Phys. Chem. B., vol. 103, pp. 1126-11255, 1999.

Desai et al., "Freestanding Carbon Nanotube Specific Fabrication", Proc. of 2005, 5th IEEE Conf., Nanotech, Nagoya, Japan, pp. 1-4, Jul. 2005.

Dillon, A. C. et al., "A Simple and Complete Purification of Single-Walled Carbon Nanotube Materials", Advanced Materials, vol. 11, No. 16, pp. 1354-1358, 1999.

Franklin, N. R. et al., "An Enhanced CVD Approach to Extensive Nanotuve Networks with Directionality", Advanced Materials, 5 pages, 2000.

Georgakilas, V. et al., "Organic Functionalization of Carbon Nanotubes", J. Am. Chem. Soc., vol. 124, No. 5, pp. 760-761, 2002.

Georgakilias, V. et al., "Purification of HiPCO Carbon nanotuubes via Organic Functionalization", J. Am. Chem. Soc., 2002, vol. 1224, pp. 14318-14319.

Haddon R.C. et al., "Purification and Separation of Carbon Nanotubes", MRS Bulletin, pp. 252-259, Apr. 2004.

Hafner, J. H. et al., "Catalytic growth of single-wall carbon Nanotubes from metal particles", Chemical Physics Letters, vol. 296, pp. 195-202, 1998.

Homma, Y. et al., "Single Walled Carbon Nanotube Growth on Silicon Substrates Using Nanoparticle Catalysts", Jpn. J. Appl. Plys., vol.. 41, Pt. 2, No. 1A/B, pp. L89-91, 2002.

Hou, P. X. et al., "Multi-step purification of carbon nanotubes", Carbon, vol. 40, pp. 81-85, 2002.

Islam, M. F. et al., "High Weight Fraction Surfactant Solubilization of Single-Wall Carbon Nanotubes in Water", Nano Letters, vol. 3, No. 2, pp. 269-273, 2003.

Johnson, R.C., "IBM Grows Nanotube Pattersn on Silicon Wafers", EETimes, 2002, 1 page.

Joselevich, E., "Vectorial Growth of Metallic and Semiconducting Single-Wall Carbon Nanotubes", Nano Letters, vol. 0, No. 0, A-E, 2002.

Kahn, M. G. C., et al., "Solubilization of Oxidized Single-Walled Carbon Nanotubes inOrganic and Aqueous Solvents through Organic Derivatization", Nano Letters, vol. 2, No. 11, pp. 1215-1218, 2002.

Vivekchand, S.R. C. et al., "A New Method of Preparing a Single-Walled Carbon Nanotube," Proc. Indian Acad. Sci., Chem-Sci. vol. 115, Nos. 5 and 6, Oct. -Dec. 2003, pp. 509-511.

Kong, J. et al., "chemical vapor deposition of methane for single-walled carbon nanotubes", Chemical Physics Letters, pp. 567-574, Aug. 14, 1998.

Kong, J. et al., "Nanotube Molecular Wires as Chemical Sensors", Science, vol. 287, pp. 622-625, Jan. 28, 2000.

Li, J. et al., "carbon Nanotube Nanoelectrode Array for Ulstrasensitive DNA Detection", Nano Lett., vol. 3, No. 5, pp. 597-602, 2003.

Li, Y. et al., "Growth of Single-Walled Carbon Nanotubes from Discrete Catalytic Nanoparticles of Various Sizes", J. Phys. Chem. B., vol. 105, pp. 11424-11431, 2004.

Li, Y. et al., "Preparation of Monodispersed Fe-Mo Nanoparticles as the Catalyst for CVD Synthesis of Carbon Nanotubes", Chem. Mater., vol. 13, pp. 1008-1014, 2001.

Matarredona, O. et al., " Dispersion of Single-Walled Carbon Nanotubes in Aqueous Solutions of the Anionic Surfactant NaDDBS", J. Phys. Chem B, vol. 107, pp.13357-13367, 2003.

Mickelson, E. T. et al., "Solvation of Fluroinated Single-Wall Carbon nanotubes in Alcohol Solvents", j. Phys. Chem. B, vol. 103, pp. 4318-4322, 1999.

Moore, V.C. et al., "Individually Suspended Single-Walled Carbon Nanotubes in Variouos Surfactants", Nano Letters, vol. 3, No. 10, pp. 1379-1382, 2003.

Murphy, R. et al., "High-Yield, Nondestructive Purification and Quantification Method for Multiwalled Carbon Nanotubes", J. Phys. Chem. b., vol. 106, pp. 3087-3091, 2002.

Nerushev, O. A. et al., "Carbon Nanotube films obtained by thermal chemical vapour deposition", J. Mater. Chem., vol. 11, pp. 1122-1132, 2001.

Niyogi, S. et al., "Ultrasonic Dispersions of Single-Walled Carbon Nanotubes", J. Phys. Chem. B., vol. 107, pp. 8799-8804, 2003.

O'Connell, M.J. et al., "Reversible Water-solubilization of Single-walled Carbon Nanotubes by Polymer Wrapping", Chem. Phys., 2001, vol. 342, pp. 265-271.

Onoa et al., "Bulk Production of singley dispersed carbon nanotubes with prescriped lenghts", Nanotechnology, vol. 16, pp. 2799-2803, 2005.

Parikh, A. et al., "Flexible vapour sensors using single walled carbon nanotubes", Sensors and Actuators B. vol. 113, pp. 55-63, 2005.

Peigney, A. et al., "A Study of the Formation of Single- and Double-Walled Carbon Nanotubes by a CVD Method", J. Phys. Chem. B., vol. 105, pp. 9699-9710, 2001.

Pompeo, F. et al., "Water Solubilization of Single-Walled Carbon Nanotubes by Functionalization with Glucosamine", Nano Letters, vol. 2, No. 4, pp. 369-373, 2002.

Qi, P., et al., "Toward Large Arrays of Multiplex Functionalized Carbon Nanotube Sensors for Highly Sensitive and Selective Molecular Detection," Nano Lett., 2003, vol. 3(3), pp. 347-351.

Riggs, J. E. et al., "Optical Limiting Properties of Suspended and Solubilized Carbon Nanotubes", J. Phys. Chem. B., vol. 104, pp. 7071-7076, 2000.

Riggs, J. E. et al., "Strong Luminescence of Solubilized Carbon Nanotubes", J. Am. Chem. Soc., vol. 122, pp. 5879-5880, 2000.

Sotiropoulos, S. et al., "Carbon Nanotube array-based biosensor", Anal. Bioanal. Chem., vol. 375, pp. 103-105, 2003.

Star, A. et al., "Preparation and Properties of Polymer-Wrapped Single-Walled Carbon Nanotubes", Angew. Chem. Int. Ed., vol. 40, No. 9, pp. 1721-1725, 2001.

Sun, Y. . et al., "High Dissolution and Strong Light Emission of Carbon Nanotubes in Aromatic Amine Solvents", J. Am. Chem. Soc., vol. 123, pp. 5348-5349. 2001.

Sun, Y. P. et al., "Soluble Dendron-Functionalized Carbon Nanotubes : Preparation, Characterization,a nd Properties", Chem. Mater., vol. 13, pp. 2864-2869, 2001.

Zhang, Y. et al., "Metal coating on suspended carbon Nanotubes and its implication to metal-tube interaction", Chemical Physics Letters, vol. 331, pp. 35-41, 2000.

Zhang, Z. et al., "Select Pathways to Carbon Nanotube Film Growth", Advanced Materials, vol. 13, No. 3, pp. 1767-1770, Dec. 3, 2001.

Zhao, Y. P. et al., "Frequency-dependent electrical transport in carbon Nanotubes", Physical Review B,. vol. 64, pp. 201402-1-201402-4, 2001.

Ago, H. et al., "Workfunction of Purified and Oxidised Carbon Nanotubes," Synthetic Metals 103 (1999) 2494-2495.

Delzeit, L. et al., "Multilayered metal catalysts for controlling the density of single-walled carbon nanotube growth," Chemical Physics Letters 348 (2001) 368-374.

Hirsch, A. "Functionalization of Single-Walled Carbon Nanotubes," Angew. Chem. Int. Ed. 2002, 41, No. 11.

International Search Report issued for International Patent Application No. PCT/US05/18465 filed May 26, 2005.

International Search Report issued for International Patent Application No. PCT/US05/18467 filed May 26, 2005.

International Search Report issued for International Patent Application No. PCT/US05/18539 filed May 26, 2005.

International Search Report issued for International Patent Application No. PCT/US05/45316 filed Dec. 15, 2005.

Jeong, T. et al., "A new purification method of single-wall carbon nanotubes using $H_2S$ and $O_2$mixture gas," Chemical Physics Letters 344 (2001) 18-22.

Martinez, M.T. et al., "Modifications of single-wall carbon nanotubes upon oxidative purification treatments," Nanotechnology 14 (2003) 691-695.

International Search Report issued for International Patent Application No. PCT/US05/17839 filed May 20, 2005.

International Search Report issued for International Patent Application No. PCT/US05/18600 filed May. 26, 2005.

Rinzler, A.G. et al., "Large-scale purification of single-wall carbon nanotubes: process, product, and characterization," Appl. Phys. A 67, 29-37 (1998).

"Wondrous World of Carbon Nanotubes," http://students.chem.tue. nl/ifp03/purfication.html, pp. 1-11, Jul. 12, 2004.

SENSOR PLATFORM USING A NON-HORIZONTALLY ORIENTED NANOTUBE ELEMENT

CROSS-REFERENCE TO RELATED APPLICATIONS

This application is a continuation of the following application, the contents of which are incorporated herein in their entirety by reference:

Sensor Platform Using a Non-Horizontally Oriented Nanotube Element (U.S. patent Ser. No. 10/844,883) filed May 12, 2004.

This application claims priority to and the benefit of the filing dates of the following:

Horizontally Oriented Sensor Constructed with Nanotube Technology (U.S. Provisional Pat. Appl., Ser. No. 60/470,410), filed May 14, 2003;

Vertically Oriented Sensor Constructed with Nanotube Technology (U.S. Provisional Pat. Appl., Ser. No. 60/470,371), filed May 14, 2003; and Resistance and Capacitance Modulation Structures Constructed with Nanotube Technology (U.S. Provisional Pat. Appl., Ser. No. 60/501,143), filed Sep. 8, 2003.

The following are assigned to the assignee of this application, and are hereby incorporated by reference in their entirety:

Nanotube Films and Articles (U.S. Pat. No. 6,706,402), filed Apr. 23, 2002;

Electromechanical Memory Array Using Nanotube Ribbons and Method for Making Same (U.S. Pat. No. 6,919,592), filed on Jul. 25, 2001;

Electromechanical Three-Trace Junction Devices (U.S. Pat. No. 6,911,682), filed on Dec. 28, 2001;

Methods of Making Carbon Nanotube Films, Layers, Fabrics, Ribbons, Elements and Articles (U.S. patent application Ser. No. 10/341,005), filed on Jan. 13, 2003;

Electro-Mechanical Switches and Memory Cells Using Vertically-Disposed Nanofabric Articles and Methods of Making the Same (U.S. Provisional Pat. Appl., Ser. No. 60/446,786) filed on Feb. 12, 2003;

Electro-Mechanical Switches and Memory Cells Using Horizontally-Disposed Nanofabric Articles and Methods of Making the Same (U.S. Provisional Pat. Appl., Ser. No. 60/446,783), filed on Feb. 12, 2003;

Patterning of Nanoscopic Articles (U.S. Provisional Pat. Appl. Ser. No. 60/501,033), filed on Sep. 8, 2003;

Patterning of Nanoscopic Articles (U.S. Provisional Pat. Appl. Ser. No. 60/503,099), filed on Sep. 15, 2003;

Non-Volatile Electromechanical Field Effect Transistors and Methods of Forming Same (U.S. Provisional Pat. Appl. Ser. No. 60/476,976), filed on Jun. 9, 2003; and Sensor Platform Using a Horizontally Oriented Nanotube Element (U.S. patent application Ser. No. 10/844,913) filed on May 12, 2004.

BACKGROUND

1. Technical Field

The present application relates generally to methods for the detection of target analytes and for measuring or detecting various electrical values by utilizing individual nanosensors and nanosensor arrays, and the application more particularly relates to means or platforms for creating such sensors and sensor arrays.

2. Discussion of Related Art

Chemical sensors and biosensors have been utilized for detecting many species, from contaminants in air (e.g., in air quality sensors) to the presence of particular DNA segments in blood samples or other samples. More recently, chemical and biosensors utilizing nanotubes, such as single-walled carbon nanotubes (SWNTs) have been proposed. Such sensors take advantage of the smaller size and greater sensitivity of the sensor. See, e.g., J. Kong et al., Science, vol. 287, pp. 622-625 (Jan. 28, 2000).

Chemical sensors made of nanotubes may be functionalized or otherwise modified to become molecule-specific or species-specific sensors, see P. Qi et al., "Toward Large Arrays of Multiplex Functionalized Carbon Nanotube Sensors for Highly Sensitive and Selective Molecular Detection," Nano Lett., vol. 3, no. 3, pp. 347-51 (2003); Dai et al., "Carbon Nanotube Sensing," U.S. patent application Ser. No. 10/175,026, filed on Jun. 18, 2002. On the other hand, such sensors may comprise non-functionalized semiconducting tubes and may sense for the presence of known chemicals, see, e.g., Kong, supra.

Because it is difficult to control the placement of individual nanotubes between electrodes, the reliable fabrication of nanoscale sensors using individual nanotubes is problematic. In addition, the nanotubes so used are singular. Thus, devices using them may stop working if a single nanotube fails at a single point.

Therefore, though a body of art and literature exists and is evolving for the use of individual nanotubes in a sensor arrangement, a need exists for a more reliable vehicle or platform to serve as a sensor.

SUMMARY

The invention relates to one or more sensor platforms and methods of making such platforms wherein sensor platforms include sensor elements oriented substantially non-horizontally—e.g., substantially vertically—with respect to a major surface of a substrate (which is understood to be "horizontal"). According to various embodiments of the present invention, a sensor element comprises one or more nanostructures such as nanotubes. According to certain embodiments, a sensor element may have or may be made to have an affinity for a corresponding analyte.

Under certain embodiments, a sensor platform includes a sensor element having a collection of nanotubes with one or more measurable electrical characteristics. A support structure supports the sensor element so that it may be exposed to a fluid, and control circuitry electrically senses the electrical characterization of the sensor element so that the presence of a corresponding analyte may be detected.

Under another embodiment of the invention, a sensor element has an affinity for the corresponding analyte.

Under another embodiment of the invention, nanotubes used are pristine nanotubes.

Under another embodiment of the invention, nanotubes are derivatized to have or to increase the affinity.

Under another embodiment of the invention, nanotubes are functionalized to have or to increase the affinity.

Under another embodiment of the invention, the sensor element has an affinity for at least two analytes and the plurality of nanotubes includes at least two types of nanotubes, a first type of nanotube having an affinity for a first analyte and a second type of nanotube having an affinity for a second analyte.

Under another embodiment of the invention, the support structure includes a channel and the sensor element is suspended to span the channel.

Under another embodiment of the invention, the support structure includes a conductive electrode positioned in the channel, and the sensor element is deflectable in response to the control circuitry to contact the electrode so that a semiconducting gating effect of the nanotubes in the sensor element may be electrically detected.

Under another embodiment of the invention, an upper electrode is positioned above and separate from the sensor element.

Under another embodiment of the invention, the sensor platform comprises a conductive element located apart from the sensor element so that the conductive element and the sensor element are in a capacitive relationship.

Under another embodiment of the invention, circuitry to measure a capacitance associated with the conductive element and the sensor element comprises an additional, reference capacitor that in turn comprises one or more nanotubes spaced apart from an additional conductive element.

Under another embodiment of the invention, the sensor platform comprises a first conductive element contacting the sensor element at a first point and a second conductive element contacting the sensor element at a second point, so that an electric current can run through the sensor element between the first and second conductive elements.

Under another embodiment of the invention, circuitry to measure the resistance between the first and second contacts to the sensor element comprises a reference resistor that in turn comprises one or more nanotubes separately contacted by conductive elements.

Under another embodiment of the invention, a large-scale array of sensor platforms is provided in which the array includes a large plurality of sensor platform cells.

Under certain embodiments of the invention, a large-scale array of sensor platforms includes a plurality of sensor elements comprising one or more nanotubes According to embodiments of the invention, sensors may be made by providing a support structure; providing one or more nanotubes on the support structure; and providing control circuitry to electrically sense the electrical characterization of the sensor element so that the presence of a selected analyte may be detected.

Under another embodiment of the invention, the sensor element has an affinity for the selected analyte.

Under another embodiment of the invention, the nanotubes are pristine nanotubes.

Under another embodiment of the invention, the nanotubes are derivatized to have or to increase the affinity.

Under another embodiment of the invention, the nanotubes are functionalized to have or to increase the affinity.

Under another embodiment of the invention, a pattern is defined with respect to a collection of nanotubes on a support structure, which pattern corresponds to a sensor element; and a portion of the fabric is removed so that a patterned collection remains on the substrate to form the sensor element having a collection of at least one nanotube and having an electrical characterization.

Under another embodiment of the invention, a collection of nanotubes is formed by growing the collection on the substrate using a catalyst.

Under another embodiment of the invention, during the growing of the nanotube collection, nanotubes are derivatized to have an affinity for a corresponding analyte.

Under another embodiment of the invention, during the growing of the nanotube collection, the nanotubes are functionalized to have an affinity for a corresponding analyte.

Under another embodiment of the invention, the nanotube collection is formed by depositing a solution of suspended nanotubes on the substrate.

Under another embodiment of the invention, the sensor elements are made of pre-derivatized nanotubes.

Under another embodiment of the invention, the sensor elements are made of pre-functionalized nanotubes.

Under another embodiment of the invention, the nanotube collection is derivatized after its growth.

Under another embodiment of the invention, the nanotube collection is functionalized after its growth.

Under another embodiment of the invention, the patterned fabric remaining on the substrate is derivatized.

Under another embodiment of the invention, the patterned fabric remaining on the substrate is functionalized.

Under another embodiment of the invention, a conductive element located apart from the sensor element is provided so that the conductive element and the sensor element are in a capacitive relationship.

Under another embodiment of the invention, circuitry to measure a capacitance associated with the conductive element and the sensor element is provided and, under certain embodiments, comprises an additional, reference capacitor that itself comprises one or more nanotubes spaced apart from an additional conductive element.

Under another embodiment of the invention, a first conductive element and a second conductive element are provided such that the first conductive element contacts the sensor element at a first point and the second conductive element contacts the sensor element at a second point, so that an electric current can run through the sensor element between the first and second conductive elements.

Under another embodiment of the invention, circuitry to measure the resistance between the first and second contacts to the sensor element is provided with a reference resistor that itself comprises one or more nanotubes separately contacted by conductive elements.

Under another embodiment, a sensor element is substantially surrounded by support structure material so that it is not substantially exposed to contact with fluid that may contain an analyte, and thus may serve as a reference element.

DETAILED DESCRIPTION

Figure 1:
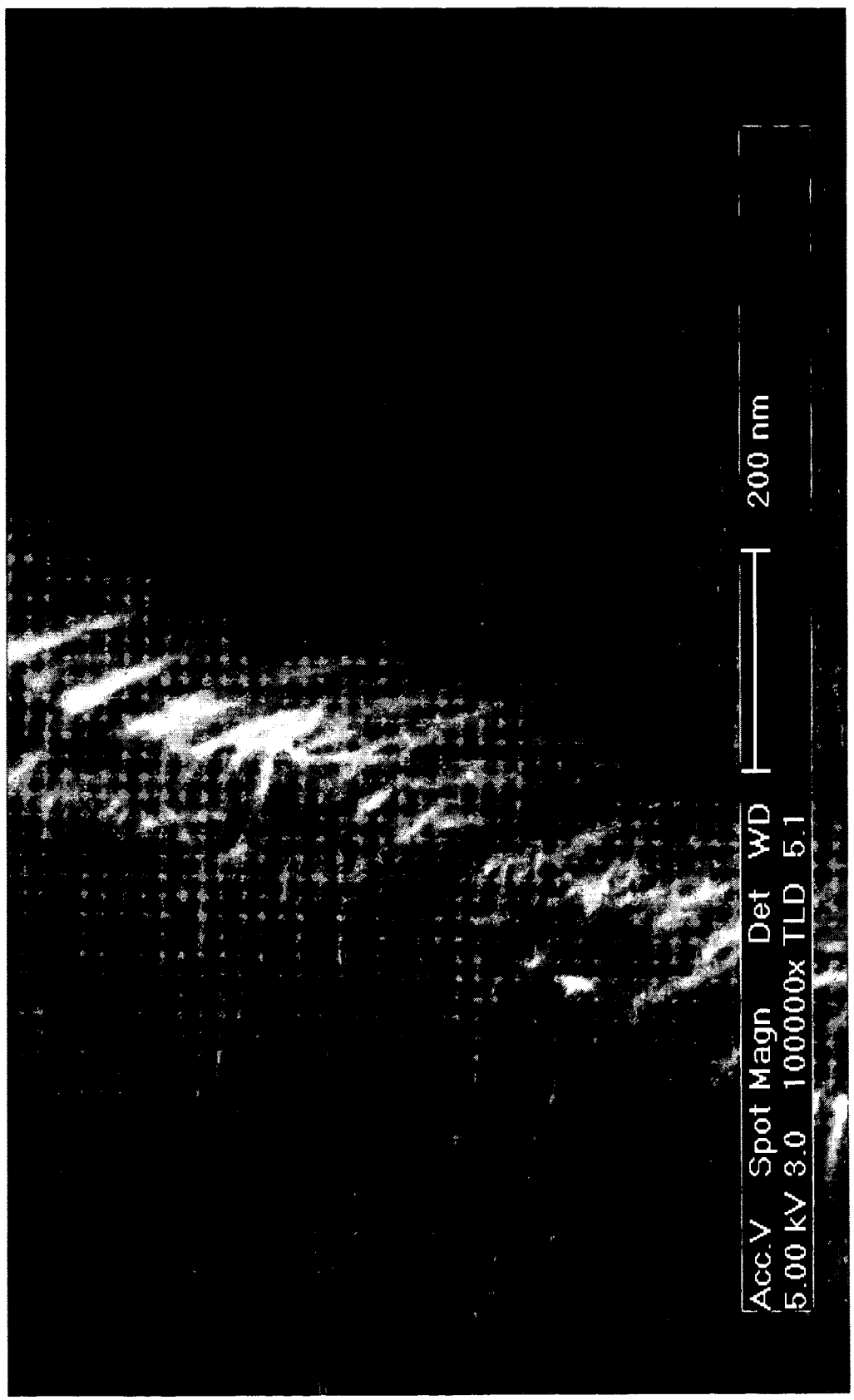
FIG. 1 is a scanning electron micrograph showing a fabric of nanotubes conforming to the surface of a substrate such that a portion of the nanotube fabric is oriented substantially perpendicularly to a major surface of the substrate.

Preferred embodiments of the invention provide a new platform or vehicle to be used in sensors and sensor arrays for biological and/or chemical sensing. They can be built using conventional semiconductor fabrication techniques and can leverage existing manufacturing infrastructure and processes to create sensors employing carbon nanotubes. The manufacturing techniques are largely compatible with CMOS processes and can be conducted at lower temperatures than those for making prior-art nanotube sensing structures. They allow fabrication of a massive number of sensors on a given chip or wafer that can be integrated with various forms of control and computational circuitry.

In certain embodiments, sensing elements are oriented substantially "vertically"—i.e., substantially perpendicular to the major surface of an associated substrate (which is understood to define the "horizontal" direction). Sensing elements may also be oriented "diagonally"—i.e., at orientations between the horizontal and vertical relative to the major surface of a substrate.

As will be described in more detail below, preferred embodiments of the invention use elements made from a fabric of nanotubes ("nanofabrics"), rather than using individual nanotubes as was suggested in prior art. These elements may be derivatized or functionalized as is taught in the art for individual nanotubes. Unlike individual nanotubes, these nanofabric elements provide a degree of redundancy (e.g., the sensor will still work even if a given tube in the element is faulty), are more easily manufactured, and may be manufactured as parts of large arrays of sensors with complementary circuitry—for example, by locating sensor elements in each of a plurality of members of an array of contact holes like that pictured in FIG. 14.

The nanofabric elements may be either unmodified or functionalized so that they may be used to detect chemical analytes, such as organic and inorganic molecules. In certain embodiments, the chemical analyte may be a biological molecule such as peptides, proteins, or nucleic acids. The nanofabric may be functionalized, either non-covalently or covalently (e.g., by derivatization) so as to interact specifically with a particular analyte. The modified or unmodified analyte-sensitive nanofabrics may be incorporated into a nanosensor device for detection of the corresponding analyte in a sample. Preferred embodiments are understood to use the principle that charge transfer between SWNTs and adsorbed molecules changes the nanotube conductance, so as to provide novel nanosensor schemes. Preferred embodiments provide methods and compositions for the detection of target analytes using changes in the conductivity of nanotube fabric upon binding of the analytes.

Sensors according to certain embodiments of the present invention can be used in a way that allows detection and measurement of differences in their conductance or other electrical properties before and after the nanotubes are bound to analytes—e.g., by interacting non-covalently or covalently with a nanotube itself or with a complex consisting of a nanotube and a functionalization agent.

The change in the sensor's electrical properties may be measured in conjunction with a gating electrode, disposed below or adjacent to the nanotubes, via a field effect on the semiconducting nanotubes, see, e.g., P. Qi et al., "Toward Large Arrays of Multiplex Functionalized Carbon Nanotube Sensors for Highly Sensitive and Selective Molecular Detection," Nano Lett., vol. 3, no. 3, pp. 347-51 (2003). When changes are detected in this way, it may be preferable to utilize a sensor with a suspended nanofabric structure.

The change in the sensor's electrical properties may also be measured via an electromechanical mechanism in which differences between switching voltage with respect to, current through, or resistance of a nanofabric element in relation to an underlying electrode is determined before and after the nanofabric is exposed to analytes. Further, the physical presence of the sensed molecules or species may result in detectable strain on the suspended nanofabric, thereby potentially allowing molecular weight of the material to be determined directly. For example, as the strain energy changes due to binding of sensed molecules, a corresponding change in voltage could be measured.

Nanosensors according to certain embodiments of the present invention are compatible with protocols that substantially prevent non-specific binding of non-target analytes. For an example of non-specific binding prevention, see Star et al., "Electronic Detection of Specific Protein Binding Using Nanotube FET Devices," Nano Lett., vol. 3, no. 4, pp. 459-63 (2003).

The nanofabric sensor of certain embodiments of the present invention may be used as an electrode in electrochemical sensors—for example, Clark-type sensors. See Lawrence et al., "A Thin-Layer Amperometric Sensor for Hydrogen Sulfide: The Use of Microelectrodes To Achieve a Membrane-Independent Response for Clark-Type Sensors," Anal. Chem., vol. 75, no. 9, pp. 2053-59 (2003).

Exemplary Architectural Sensor Platforms

FIGS. 2(A)-(E) illustrate various embodiments of the invention. As will be described below, the sensor platforms may provide a vehicle in which a nanofabric element may be derivatized or functionalized after fabrication of the platform, but, in some embodiments, the derivatization or functionalization of the nanofabric element may be incorporated into the manufacturing steps of forming the sensor platform. In FIGS. 2(A)-(E), an individual sensor cell is shown, but, as will be clear from the description below, the utilization of well-known semiconductor manufacturing techniques allows these individual sensor cells to be replicated on a massive scale so that a given chip or wafer may have a very large number of sensors that may be essentially identical to one another. The cells may be organized into massive arrays, small groups, or individual entities. The description focuses on the architecture and basic platform. Subsequent sections discuss how the properties of the nanofabric element may be tailored in specific ways to achieve specific desired effects.

The nanofabric element 202 of certain embodiments is formed from a non-woven fabric or layer of matted nanotubes (described in more detail below, and also described in incorporated references). Under certain embodiments, the fabric is formed of single-walled carbon nanotubes (SWNTs), but other embodiments may utilize multi-walled carbon nanotubes (MWNTs) or mixtures of single- and multi-walled carbon nanotubes or other nanoscopic elements, such as nanowires. The fabric of certain embodiments is substantially a monolayer of nanotubes with substantially constant porosity. This porosity may be substantially determined by, for example, the number and density of spin coats, which commonly also plays a principal role in substantially determining the capacitance of a particular nanofabric.

The sensing parameters of the nanofabric element resemble those of individual nanotubes. Thus, the predicted sensing times and switching voltages for the nanofabric element should approximate the corresponding times and voltages for individual nanotubes. Unlike prior art which relies on directed growth or chemical self-assembly of individual nanotubes, preferred embodiments of the present invention utilize fabrication techniques involving thin films and lithography. Such methods of fabrication lend themselves to generation of nanotubes and nanotube material over large surfaces, such as wafers 300 mm in diameter. (In contrast, growing individual nanotubes over a distance beyond the sub-millimeter range is currently unfeasible.) The nanofabric element should exhibit improved fault tolerances over individual nanotubes, by providing redundancy of conduction pathways through nanofabric elements. (If an individual nanotube breaks, other tubes within the fabric can provide conductive paths, whereas, if a sole nanotube were used and broken, the associated nanosensing cell would be faulty.) Moreover, the resistances of nanofabric elements should be significantly lower than those for individual nanotubes, thus decreasing their impedance, since a nanofabric element may be made to have larger cross-sectional areas than individual nanotubes.

While typically a monolayer fabric of single-walled nanotubes may be desirable, for certain applications it may be desirable to have multilayer fabrics to increase current density or redundancy, or to exploit other mechanical or electrical characteristics of a multilayer fabric. Additionally, for certain applications it may be desirable to use either a monolayer fabric or a multilayer fabric comprising multi-walled nanotubes or comprising a mixture of single-walled and multi-walled nanotubes.

A nanosensor crossbar junction may be formed by a crossing of nanotubes and an electrode. Appropriate application of voltages to such a system can result in deflection of the nanotubes toward or away from the electrode, and, in certain embodiments, can result in a bistable junction with a pair of "on" or "off" states—states in which the nanotubes are in stable positions of contact (e.g., electrical or physical) with the electrode or separation from the electrode, respectively.

Figure 2A:
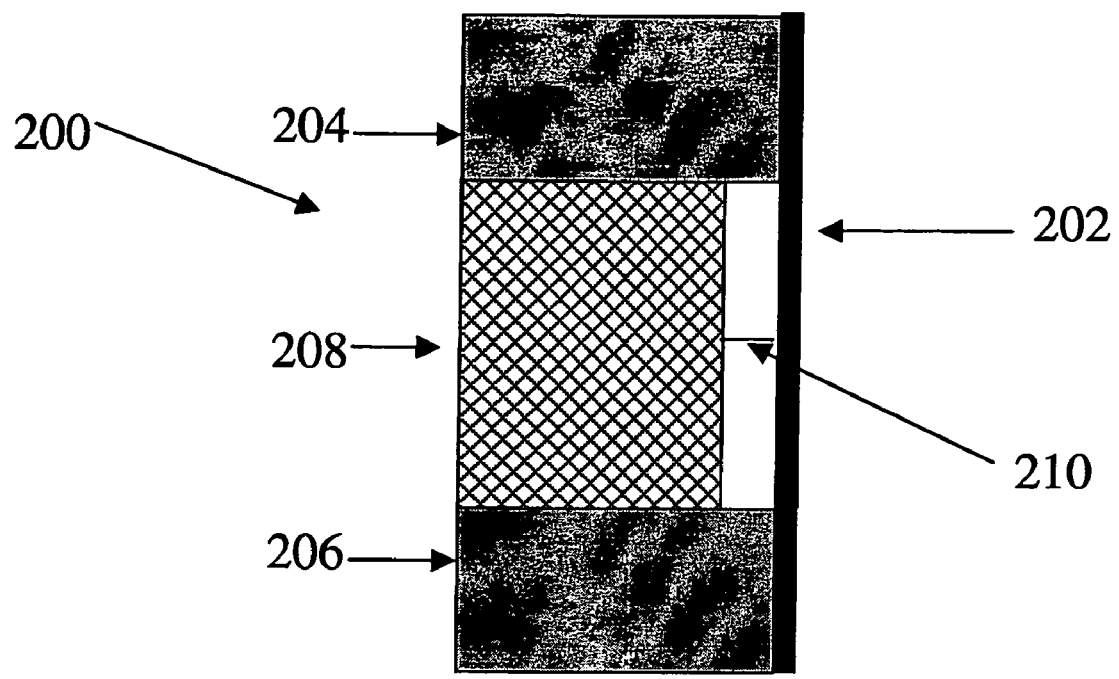
FIGS. 2(A)-(E) illustrate nanotube fabric sensor devices according to certain embodiments of the invention.

FIG. 2(A), for example, illustrates an exemplary platform (or sensor cell) 200 in cross-sectional view. Platform 200 includes a nanofabric element 202 that rests on or is pinned to supports 204 and 206. The element is suspended over an electrode 208 by a gap distance 210.

Figure 2B:
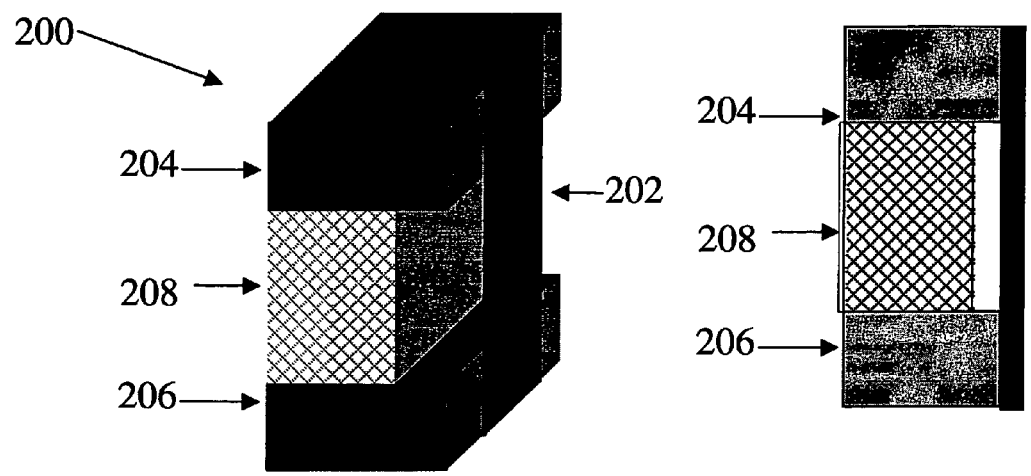
Figure 2C:
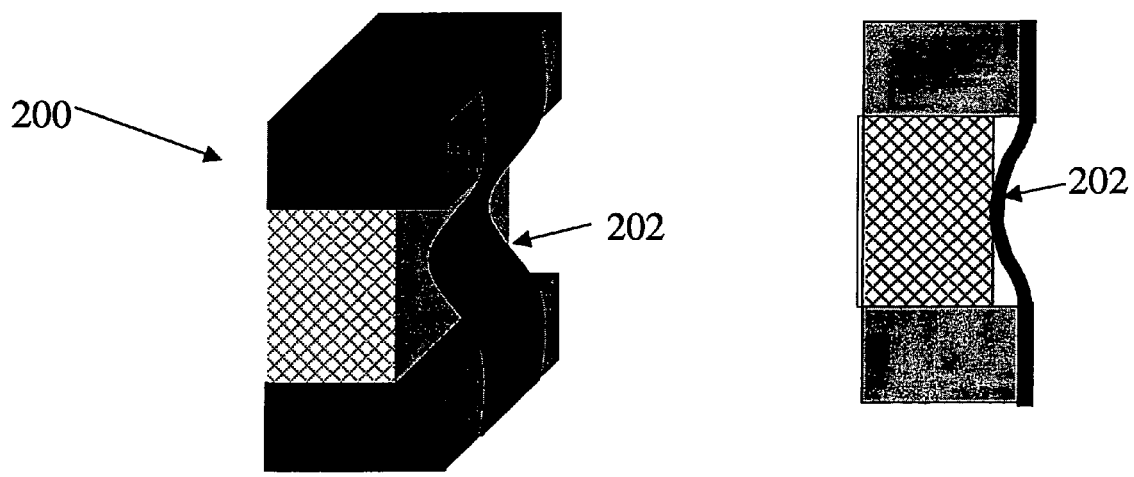

Two states of the nanofabric element 202 are shown with the perspective views of FIGS. 2(B)-(C). FIG. 2(B), for example, shows the platform in an undeflected state, and FIG. 2(C) shows the platform in a deflected state in which the nanofabric element has been caused to deflect into contact with electrode 208. Switching between the states is accomplished by the application, or removal, of specific voltages across the nanofabric element 202 and one or more of its associated electrodes 208. Switching forces are based, in part, on the interplay of electrostatic attraction and repulsion between the nanofabric article 202 and the electrode 208. Under certain circumstances, the second state of contact between nanofabric and electrode is "volatile": e.g., the nanofabric moves into contact with the electrode only when voltage is applied, and returns to its undeflected state when the voltage is removed. Under different circumstances, the state of contact is "nonvolatile": e.g., it may initially result from application of a voltage, but it continues after that voltage is removed.

Methods to increase adhesion energies between nanotubes and the electrode surface can be envisioned, and could involve the use of ionic, covalent, or other forces. These methods can be used to extend the range of bistability for nanotube-electrode junctions.

Upon successful completion of the sensing activity, it may be desirable to be able to reset a device in the field. In order to accomplish such a reset, it is possible that an electrical pulse able to cause removal of a sensed molecule from a nanosensor could be provided to clear or zero the state of the sensor. Necessary voltages could be determined for individual sensor types specifically or could be part of an overall reset pattern which might simultaneously clear all of the sensors from their states at a particular time. Such a reset feature would allow sensors to become saturated but then to be returned to their original state so that the device could be reused. Reusability would reduce overall cost and maintenance requirements.

Under certain embodiments, the electrode 208 may be used as a reference or as a field generator involved in measurement. A "reference" electrode could be used to prevent false positive or false negative readings by creating a comparison between a "sense" cell and a non-binding cell.

Under certain embodiments, each cell may be read by applying currents and/or voltages to nanofabric articles 202 and/or the electrode 208. The electrical properties of the sensor may then be measured (measuring apparatus is not shown). For example, the nanofabric element 202 may contact the underlying electrode 208 and remain in contact, in a nonvolatile state. As a result, a change in the resistance or other electrical properties of the element 202, resulting from analyte binding—for example, a gating effect—may be detected. See P. Qi et al., "Toward Large Arrays of Multiplex Functionalized Carbon Nanotube Sensors for Highly Sensitive and Selective Molecular Detection," *Nano Lett.*, vol. 3, no. 3, pp. 347-51 (2003).

In certain embodiments, the support structures 204 and 206 are made from silicon nitride ($Si_3N_4$) and are separated by about 180 nm. Meanwhile, the gap distance 202 is approximately 5-50 nm. Such a 5-50 nm gap distance is preferred for certain embodiments utilizing nanofabrics made from carbon nanotubes, and reflects the specific interplay between strain energy and adhesion energy for the deflected nanotubes. Gap distances of about 5-50 nm commonly create a platform in which a deflected state is retained in a nonvolatile manner, meaning the element 202 will stay deflected even if power is removed from the electrodes. Other gap distances may be preferable for other materials. Larger gap distances may be used to create volatile behavior, meaning that the deflected state will be lost when power is interrupted.

The electrode 208 may be made of any suitable electrically conductive material and may be arranged in any of a variety of suitable geometries. Certain preferred embodiments utilize n-doped silicon to form such a conductive element, which can be, preferably, no wider than the nanofabric article 202, e.g., about 180 nm in width or less. Other embodiments utilize metal as conductor. In certain embodiments, the electrode 208 can be constructed from a nanofabric.

Likewise, the material of the support structures 204 and 206 may be made of a variety of materials and in various geometries, but certain preferred embodiments utilize insulating material, silicon nitride, or silicon oxide, and certain embodiments utilize electronic interconnects embedded within one support structure or both.

In certain embodiments, the element 202 is held to the insulating support structures by friction. In other embodiments, the nanofabric article 202 may be held by other means, such as by anchoring the nanofabric to the support structures using any of a variety of techniques. Evaporated or spin-coated material such as metals, semiconductors or insulators especially silicon, titanium, silicon oxide, or polyimide can be added to increase the pinning strength. The friction interaction can be increased through the use of chemical interactions, including covalent bonding through the use of carbon compounds such as pyrenes or other chemically reactive species. See R. J. Chen et al., "Non-covalent Sidewall Functionalization of Single-Walled Carbon Nanotubes for Protein Immobilization," *J. Am. Chem. Soc.*, vol. 123, pp. 3838-39 (2001), and Dai et al., *Appl. Phys. Lett.*, vol. 77, pp. 3015-17 (2000), for exemplary techniques for pinning and coating nanotubes by metals. See also WO 01/03208 for discussion of such techniques.

Specifically, for example, the nanofabric article 202 may be coupled to another material by introducing a matrix material into the spaces between the nanotubes in a porous nanofabric to form a conducting composite junction, as described in the references incorporated above. Electrical and mechanical advantages may be obtained by using such composite junctions and connections. In one example, a conducting material is deposited onto the nanofabric and is allowed to penetrate into the spaces within the porous nanofabric, thus forming an improved electrical connection to the nanofabric and reducing the nanofabric article's contact resistance. In another example, an insulating material is deposited onto the nanofabric and is allowed to penetrate into the spaces within the porous nanofabric, thus forming an improved mechanical pinning contact that increases strain when the article is bent or deflected.

FIG. 2(C) illustrates a deflected nanofabric sensing switch according to one embodiment of the invention. The electrode or conductive trace 208 is disposed near enough to the suspended portion of the nanofabric element 202 that the two may contact one another when the nanofabric is deflected. The electrode 208 may also operate to create a field that can alter the electrical properties of a nearby nanofabric sensor; more particularly, the electrode 208 may create a field that alters the properties of semiconducting nanotubes in a nanosensor cell such as that of FIG. 2(B). It is therefore an object of certain embodiments of the invention to create a nanofabric sensor composed substantially or entirely of semiconducting nanotubes disposed adjacent to a field-emitting electrode. See P. Qi et al., "Toward Large Arrays of Multiplex Functionalized Carbon Nanotube Sensors for Highly Sensitive and Selective Molecular Detection," *Nano Lett.*, vol. 3, no. 3, pp. 347-51 (2003).

Figure 2D:
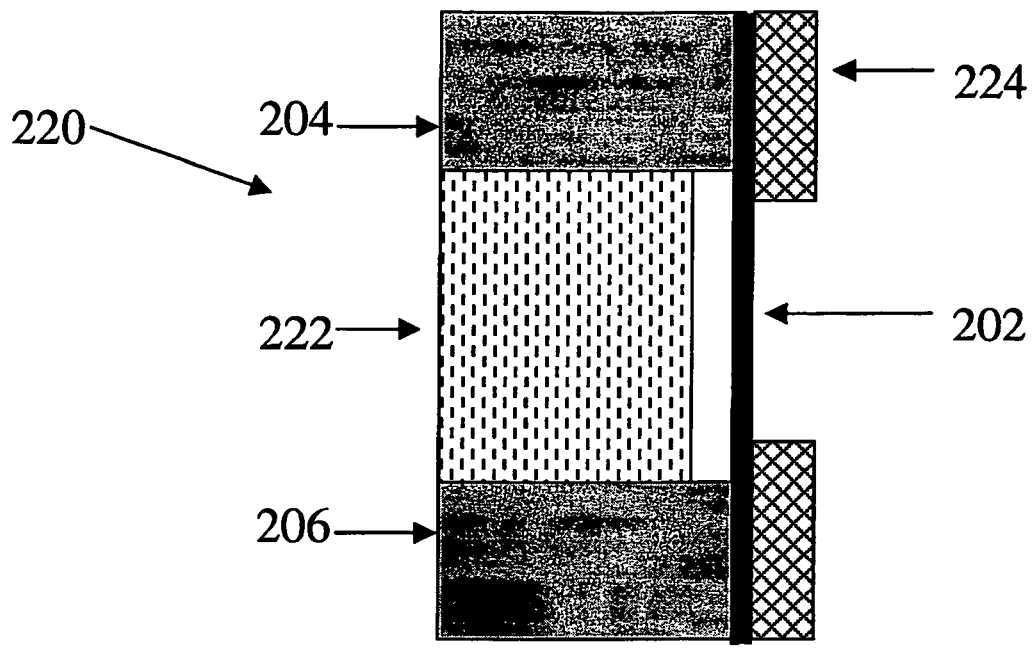

FIG. 2(D) illustrates another nanosensor cell 220. In this embodiment, the electrode 208 of platform 200 is replaced with a nonmetal material 222 disposed adjacent to the suspended portion of the nanotube fabric 202. Pinning structures 224, mentioned above, are shown explicitly in this case. Such pinning structures can allow facile electrical connection to the nanofabric as well as providing support or clamping of the nanofabric to the underlying surface 204. Pinning structures would be conductive in many applications, but can be insulating or conductive, depending on the application.

Figure 2E:
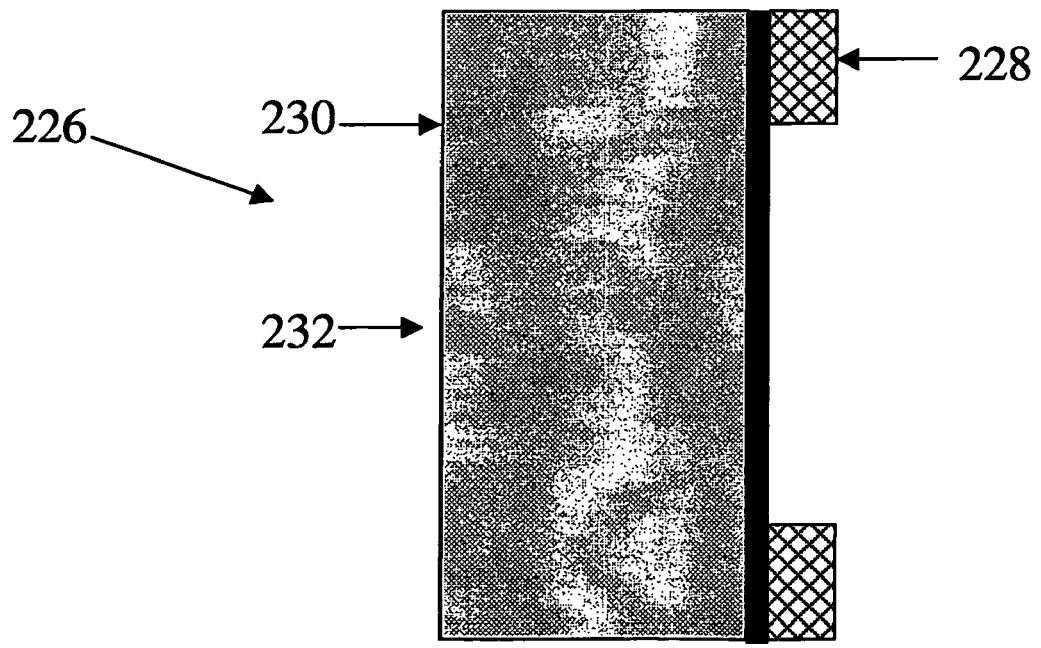

FIG. 2(E) illustrates another nanosensor cell 226. In this embodiment, the nanofabric element 202 is not suspended and instead rests upon support material 230. Support material 230, which may also be characterized as a pinning structure, may be anything consistent with use as a sensor, including but not limited to metals, alloys, ceramics, semiconductors, plastics, glass etc. Such a pinning structure can allow facile electrical connection to the nanofabric as well as providing support or clamping of the nanofabric to the underlying structure 204. A pinning structure would in many cases be conductive, but can be insulating or conductive, depending on the application.

Figure 3A:
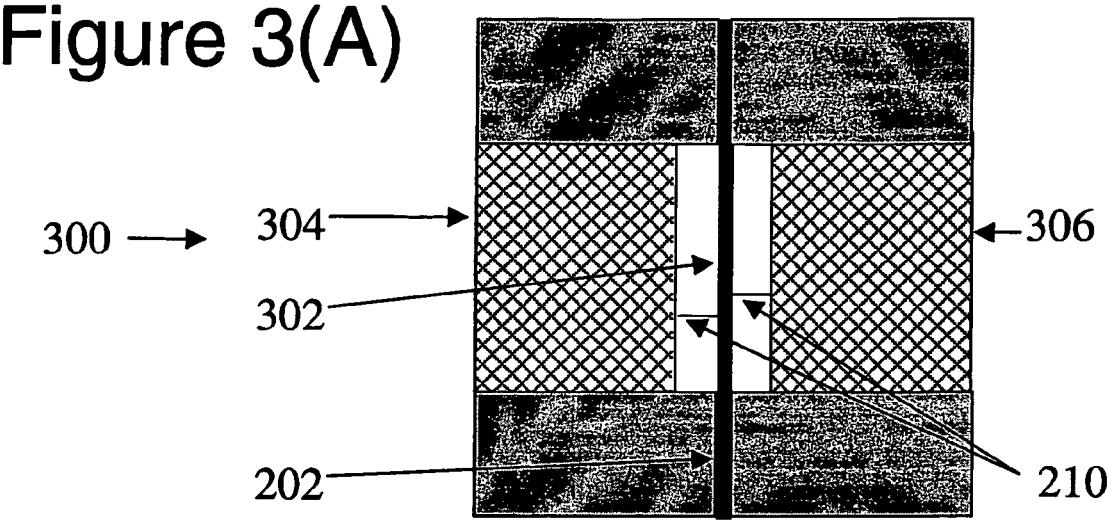
FIGS. 3(A)-(C) illustrate nanotube fabric sensor devices according to certain embodiments of the invention.
Figure 3B:
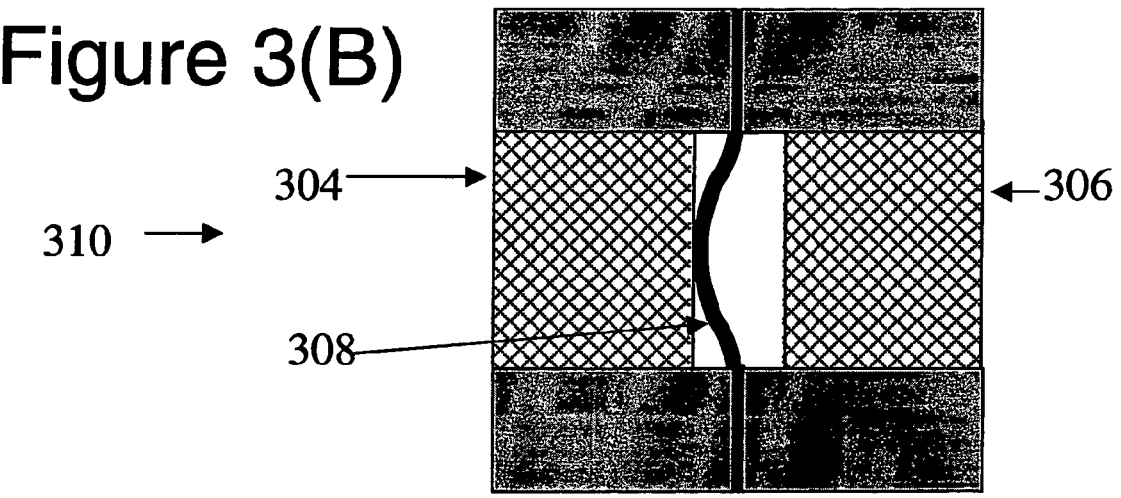
Figure 3C:
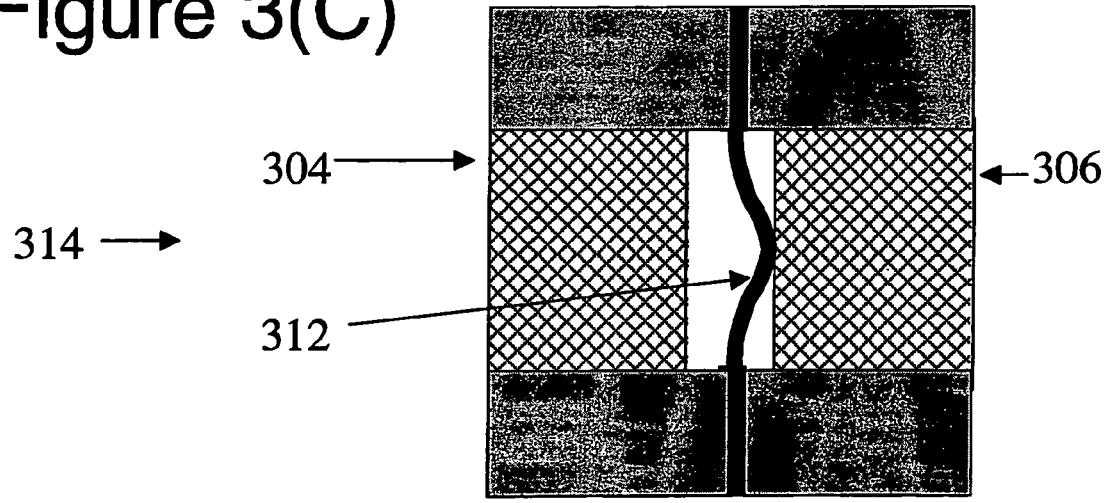

FIGS. 3(A)-(C) illustrate another sensor cell and the states such a cell might achieve. In this cell, the nanofabric element 202 is positioned between a lower electrode 304 and upper electrode 306. The electrodes 304 and 306 (together with element 202) may be electrically stimulated to deflect the element 202 toward and away from electrode 304. For example, in some embodiments, the element 202 may be caused to deflect between the "at rest" state of FIG. 3(A) and the deflected state of FIG. 3(B). In certain embodiments, such a deflected state may be characterized as an "on" state in which the nanofabric-electrode junction is an electrically conducting, rectifying junction (e.g., Schottky or PN), which may be sensed as such through either the nanofabric article or the electrode 304, when addressed. In certain embodiments where the cell may be in a third state, as illustrated by structure 314 of FIG. 3(C), the nanofabric article 202 may be deflected toward electrode 306 generating an "on" state different from the "on" state of the previous example (relevant electrical properties may be the same in both "on" states, but are addressed by different electrodes).

It should be recognized that figures such as FIGS. 3(A)-(C) are not drawn to scale, and the gap distances 210 in a given cell, for example, need not be equal. In other embodiments, the gap on one side of a nanofabric article 202 may be different from that on the other side, potentially to allow various combinations of volatile and nonvolatile switching behavior. Moreover, inclusion of a third trace in the form of a release node can add a capacity to use this third trace to reset the cell or to isolate a particular cell. For example, a voltage could be applied to a third trace to isolate a cell by causing a nanofabric article to be held in a particular nonvolatile state.

Furthermore, advantages in increased reliability and defect tolerance can come from the redundancy permitted by the presence of two conductive electrodes 304 and 306. Each of the two conductive electrodes may be separately used to apply forces to move an electromechanically responsive nanofabric element, and each of the two conductive electrodes may serve as the "contact" for one of two alternative "on" states. Thus, the failure of one conductive trace may not be fatal to sensor junction performance. Among other things, the structures as shown in FIG. 3 generally facilitate packaging and distribution, and allow nanotube-technology cells to be more easily incorporated into other circuits and systems such as hybrid circuits. The nature of the electrical architecture can also facilitate the production of stackable sensor layers and the simplification of various interconnects.

Techniques for Tailoring Characteristics of Nanofabric Element

Monolayer nanofabrics are made from single- or multi-walled nanotubes. The electrical properties of nanofabrics are highly tunable depending upon concentration of nanotubes within a given fabric. These characteristics can be controlled. For example, by selecting the proper length and width of a nanotube fabric as well as its porosity, a specific resistance per square can be measured in a range from 1-1000 kOhm/□ up to 1-10 megaOhm/□ depending upon the type of device required and its necessary characteristics. Lower resistances may be achieved by shrinking the nanofabric dimensions and placing the nanofabric in contact with metal. Certain devices where the concentration of sensors must be higher might require a lower resistance nanofabric.

A more sensitive device (e.g., one that uses fewer nanotubes in the nanofabric) would require fewer binding sites for specific analytes and could have a higher resistance. Many specific methods of preparing the nanofabric can be envisioned, depending upon the specific sensing requirements for a particular device. Tuning methods of production, and the resulting products, to device requirements can be performed by using a combination of spin coating and photolithography in conjunction with functionalization or derivatization as described herein.

Nanofabrics may be created by chemical vapor deposition (CVD) or by applying prefabricated nanotubes onto a substrate (e.g., spin coating). Various exemplary techniques are described in the incorporated and/or published patents and patent applications identified above.

In the event that CVD-grown nanotubes are to be utilized, derivitazation or functionalization of the fabric are straightforward. A CVD-grown nanofabric can be derivatized or functionalized in the same fashion as the spin-coated fabric. Nanotubes grown by CVD can be doped during the growth process with a limited number of materials such as boron, silicon, indium, germanium, phosphorous, arsenic, oxygen, selenium, and other monatomic species using current technologies. After the CVD process has been completed, CVD-grown nanotubes can be easily doped with an even wider variety of materials, including many types of molecules—for example, chemicals, drugs, DNA, RNA, peptides, or proteins.

The fabrication of nanofabrics by spin coating pre-formed nanotubes is described in the incorporated and/or published patents and patent applications identified above. Such an approach has advantages over fabrication of nanofabrics by CVD. For example, lower temperatures may be used for manufacture of the device. This allows more materials to be used as a potential substrate in conjunction with the nanofabric element. In addition, prefabricated nanotubes may be derivatized or functionalized with nearly limitless agents before the nanotubes are applied to a substrate.

Other techniques for forming the nanofabric may be used as well—e.g., aerosol application, dipping, or any other appropriate method.

Nanofabric sensors may be comprised of semiconducting nanotubes, metallic nanotubes or both. Investigators have shown that metallic nanotubes may be separated from semiconducting nanotubes by precipitation. See, e.g., D. Chattopadhyay et al., "A Route for Bulk Separation of Semiconducting from Metallic Single-Walled Carbon Nanotubes," *J. Amer. Chem. Soc.*, vol. 125, pp. 3370-75 (Feb. 22, 2003). It is therefore an aspect of certain embodiments of the present invention to create nanofabrics of controlled composition (semiconducting vs. metallic) using this or any other method of separation. According to one precipitation method, single-walled nanotubes are acid-treated and then functionalized non-covalently—e.g., in octadecylamine and tetrahydrofuran—causing metallic species to precipitate out of solution while leaving semiconducting nanotubes in solution. Either of the separate lots of nanotubes may be used for nanofabric creation once they are separated from one another. Separated nanotubes may be used to create nanofabrics for use as nanosensors with or without functionalization, and such nanotubes may be used in spin-coating applications and other appropriate methods as explained herein and in incorporated references. Furthermore, the relative concentrations of semiconducting and metallic nanotubes may be controlled. For example, one may create a fabric of approximately 90% semiconducting tubes and 10% metallic nanotubes by mixing a solution of 100% semiconducting nanotubes with a solution of unseparated nanotubes to acquire the desired concentration of each type of nanotube. Solutions of 100% semiconducting tubes may be mixed with solutions of 100% metallic nanotubes as well.

Metallic nanotubes may also be destructively eliminated from already-formed nanofabrics by current-induced oxidation, see, e.g., P. G. Collins et al., "Engineering Carbon Nanotubes and Nanotube Circuits Using Electrical Breakdown," *Science*, vol. 292, pp. 706-09 (2001). It is an aspect of certain embodiments of the present invention to utilize the protocols set forth in this reference to create a nanofabric and to apply an appropriate voltage to it in order effectively to burn away metallic nanotubes. This method will work with nanofabrics that are created by CVD or by any other process, such as spin coating, etc.

Once formed, the nanofabric can be patterned by using standard lithography techniques, as described in the incorporated and published patent references. Such lithography techniques allow patterning of nanofabric by permitting the controlled definition of a region of fabric for use as a sensor element—for example, in the form of a nanotube ribbon of substantially predetermined dimensions.

Exemplary Types of Sensors that may be Made Using the Sensor Platforms of Preferred Embodiments A nanosensor can be composed of carbon nanotubes or other highly robust materials, including nanowires, that can operate under extreme conditions with no loss of sensitivity. Four general types of nanosensors have been envisioned:

pristine nanotubes (i.e., non-functionalized nanotubes)
non-covalently functionalized nanotubes
covalently derivatized nanotubes
a hybrid mixture of above.

1. Non-Functionalized, or Pristine, Nanotubes

The first type of sensor utilizes pristine nanotubes in the nanofabric element—that is, the nanotubes are non-functionalized nanotubes. The surfaces of the nanotubes will adsorb analytes, which can alter electrical properties of the nanotubes, such as nanotube conductance or capacitance.

Under this approach, nanotubes may adsorb molecules or species onto their surfaces, resulting in a measurable change in electrical characteristics, such as a change in conductivity, resistance, capacitance, etc. The change in electrical characteristic(s) may be measured directly from the nanotubes themselves via an appropriate electrical contact.

Nanosensors can be used to detect concentrations of specific, known molecules. See L. Valentini et al., "Sensors for Sub-ppm $NO_2$ Gas Detection Based on Carbon Nanotube Thin Films," *Appl. Phys. Lett.*, vol. 82, no. 6, pp. 961-63 (2003). It is therefore an aspect of certain embodiments of the present invention to use nanofabric sensors to detect such concentrations.

2.-4. Functionalized Nanotubes

Before nanotubes are applied to a surface to create a nanofabric, they can be functionalized in solution in order to increase the bonding of the tubes to a surface and/or to make possible the bonding of, or interaction with, analytes. It is therefore an object of certain embodiments of the present invention to functionalize individual nanotubes before they are used to create a nanofabric. It is a further object of certain embodiments of the present invention to use such functionalized nanotubes to create nanosensors, especially by patterning the nanofabric into specific shapes.

Nanotubes may be functionalized in suspension before they are used to create a nanofabric, and such functionalized tubes may be stored in bulk before use. Such bulk-functionalized nanotubes may be mixed with pristine nanotubes to generate a partially functionalized nanofabric. More than one variety of functionalized nanotube solutions may be combined to generate mixtures of nanotubes to make mixed-functionalized nanofabrics. This procedure can be repeated to generate nanofabrics having as many different species of functionalized nanotubes as is desired for sensing. Thus, one could, for example, functionalize a nanotube solution with DNA sequences to sense from a test sample just particular species of interest, such as those associated only with a specific virus or solely with specific forms of cancer. An aspect of certain embodiments of the present invention is the use of nanosensors in the detection of specific antigens or major histocompatibility complex (MHC)/antigen complexes from mixtures of fluids to be tested as an early warning sensor of disease or infection.

In another embodiment, nanotubes may be functionalized after nanotubes have been applied to a substrate in order to create a nanofabric. In this case, solution or gas phase functionalization could proceed before or after patterning the nanofabrics. This technique would lend itself to multiple spatially-addressable functionalization events across a surface. For example, one could envision using an inkjet-like process to spray various types of functionalizing agents onto specific regions of a substrate. Subsequent steps could be used to apply additional functional groups in the same or different regions to make nanosensor devices with regionally tailored sensing agents on the same substrate. In this way, many different types of analytes could be sensed by a given array, potentially with each cell sensing for the presence of a different analyte.

In yet another embodiment, nanotubes may be functionalized after sensing regions are patterned out of the bulk nanofabric. (See U.S. patent application Ser. Nos. 10/341,005, 10/341,055, 10/341,054 and 10/341,130 for exemplary details on creating and patterning fabrics.) Upon completion of patterning, individual regions can be functionalized to serve as specific sensors. Multiple serial functionalizations or mixtures of functionalizing agents can be used to generate hybrid sensors capable of sensing more than one analyte at a time on a patterned nanofabric section or many such sections. This property lends itself to automation and use with robotics.

Suitable analytes include organic and inorganic molecules, including biomolecules. In a preferred embodiment, the target analyte may be

- any environmental pollutant(s), including pesticides, insecticides, toxins, etc.;
- a chemical or chemicals, including solvents, polymers, organic materials, etc.;
- one or more types of therapeutic molecules, including therapeutic and abused drugs, antibiotics, etc.;
- one or more types of biomolecules, including hormones, cytokines, proteins, lipids, carbohydrates, cellular membrane antigens and receptors (neural, hormonal, nutrient, and cell surface receptors) or their ligands, etc;
- whole cells, including prokaryotic (such as pathogenic bacteria) and eukaryotic cells, including mammalian tumor cells;
- viruses, including retroviruses, herpes viruses, adenoviruses, lentiviruses, etc.; and
- spores; etc.

For example, potential analyte molecules include nucleic acids, oligonucleotides, nucleosides, and their grammatical equivalents, as well as any and all modifications and analogs thereof, as understood in the art—including, for example, amino- or thio-modified nucleosides, and nucleotide molecules with alternate backbones or containing one or more carboxylic sugars, see, e.g., Beaucage et al., *Tetrahedron*, vol. 49, no. 10, p. 1925 (1993); Jenkins et al., *Chem. Soc. Rev.*, pp. 169-176 (1995). Hence, quite generally, molecules having at least two nucleotides covalently linked together could be potential analytes. Further, the category of potential analytes encompasses both single-stranded and double-stranded nucleic acids, as well as nucleic acids containing portions of both double-stranded and single-stranded sequences. Similarly, a potential nucleic-acid analyte could be DNA (including genomic or cDNA), RNA, or a hybrid, where the nucleic acid contains any combination of deoxyribo- and ribo-nucleotides, and any combination of bases, including uracil, adenine, thymine, cytosine, guanine, inosine, xathanine, hypoxathanine, etc. Mimetic compounds for any of the above might also act as potential analytes. In like fashion, potential analytes include proteins, oligopeptides, peptides, and their analogs, including proteins containing non-naturally occurring amino acids and amino-acid analogs, and peptidomimetic structures.

One skilled in the art will understand that a large number of analytes may be detected using embodiments of the present invention. Any target analyte for which a binding ligand, described herein, may be made may be detected using the methods and articles of certain embodiments of the invention.

Nanoimprint lithography may be used as a method of applying functionalization agents to discrete portions of nanofabric and thus to create discrete nanosensors. Such a method is primarily used for making massive arrays with sub-100 nm features. Inkjet printing technology may be used for applying functionalization agents to discrete portions of a nanofabric to create separate nanosensors on a given wafer. Inkjet printing can be used to automate the functionalization of discrete nanosensor cells, either by applying functionalization agent to nanofabric cells directly, or by applying functionalized nanotubes to the area where a cell would reside on a substrate. Inkjet printing is a non-impact, dot-matrix printing technology in which droplets of ink or, in this case, nanotube solutions are "jetted" from a small aperture directly to a specified position on a surface or medium to create an image.

Investigators have described a way of immobilizing proteins at specific locations on nanotubes. See I. Banerjee et al., "Location-Specific Biological Functionalization on Nanotubes: Attachment to Proteins at the Ends of Nanotubes Using Au Nanocrystal Masks," *Nano Lett.*, vol. 3, no. 3, pp. 283-287 (2003). Certain embodiments of the current invention utilize the teachings of Banerjee in that nanosensors can be made using proteins immobilized at the ends of nanotubes to sense for complementary species. According to this method, nanocrystals of gold are applied to the sidewalls of nanotubes, and avidin is adsorbed onto the entire surfaces of the nanotubes. A chemical etch procedure is performed to remove the gold nanocrystals and therefore also remove the avidin overlying the gold nanocrystals, leaving only the avidin attached to the ends of the nanotubes. It is therefore an aspect of certain embodiments of the present invention to fabricate nanosensors using this procedure and to immobilize protein at the ends of nanotubes used in nanosensing cells, articles, and elements.

The sensors should be exposed to analytes, either as a part of a fully or nearly fully exposed system or as part of an encapsulated system whereby analytes are introduced in a controlled way. For example, the nanofabric of a gas sensor may be fully exposed to the air, whereas the nanofabric of a DNA sensor might be encapsulated within a complex microfluidic analyte introduction mechanism. With regard to the latter, see PCT publication WO 00/62931, "The Use of Microfluidic systems in the Electrochemical Detection of Target Analytes." In this PCT document, the inventors describe a sensor system whereby a fluid containing analytes is introduced to a sensing chamber by way of microchannels. Optional storage chambers and cell lysing chambers may be connected to the system by way of other microchannels. It is an object of certain embodiments of the present invention to utilize nanofabric sensors in such microfluidic systems.

Another such microfluidic analyte delivery system is described in U.S. Pat. No. 6,290,839 to Kayyem, wherein a detection surface comprises a detection electrode having a monolayer of conductive oligomers, and optionally a capture binding ligand capable of binding the target analyte. The target analyte directly or indirectly binds to the capture binding ligand to form a binding complex. The binding complex further comprises at least one electron transfer moiety. The presence of the electron transfer moiety is detected using the detection electrode. It is therefore an object of certain embodiments of the present invention to use the nanofabric sensor as the sensing element in the device according to the '839 patent to Kayyem.

The nanosensor according to certain embodiments of the present invention may also be used as a detector according to the principles disclosed in U.S. Pat. No. 6,361,958 to Sheih. Sheih relates to a microfluidic device with microchannels that have separated regions that have a member of a specific binding pair member such as DNA or RNA bound to porous polymer beads or structures fabricated into the microchannel. Microchannels of embodiments of the invention are fabricated from plastic and are operatively associated with a fluid propelling component and detector. It is therefore an aspect of certain embodiments of the present invention to incorporate a nanosensing fabric into the system of the '958 patent to Sheih.

The nanosensors according to certain embodiments of the present invention may also be used for analyte delivery and detection in conjunction with the nanofluidic channels described in incorporated references.

2. Non-Covalent Functionalization

The second type of sensor utilizes a nanofabric element in which nanotube surfaces are non-covalently functionalized. This allows for interaction with a wide variety of cations, anions, metal ions, small molecules, DNA, and proteins.

Non-covalent functionalization takes advantage of non-covalent bonding of molecules to the sidewalls of nanotubes with substantial retention of the chemical structure and electrical characteristics of the nanotubes. Nanosensing devices can take advantage of such functionalization of nanotubes to increase, or make possible, bonding of nanotubes to analyte molecules or atoms. Nanofabrics may be non-covalently functionalized by adding pyrenes or other chemicals that are known to bind to nanotubes or graphite. For example, 1-pyrenebutanoic acid and succinimidyl ester in organic solvent, such as dimethylformamide or methanol, can be used to generate a succinimydyl functionalized nanotube. This method takes advantage of the pyrenyl group's interaction with the sidewalls of the nanotubes while generating succinyl ester groups that are highly reactive with nucleophilic substitution by primary and secondary amines found on the surfaces of most proteins and peptides as well as many drug and pro-drug compounds—where a "pro-drug" is, for example, an inactive precursor of a drug that is converted into active form in the body by normal metabolic processes. This functionalization mechanism is used to immobilize proteins and a wide variety of other biomolecules onto the sidewalls of SWNTs and to sense specifically for molecules that conjugate or bind those immobilized molecules preferentially. For example, streptavidin may be adsorbed onto a nanotube surface in order to be used in immunohistochemical sensing. See Chen et al., "Non-covalent Sidewall Functionalization of Single walled Carbon Nanotubes for Protein Immobilization," *J. Am. Chem. Soc.*, vol. 123, pp. 3838-39 (2001). The use of such nanosensors is compatible with analyte detection systems where non-specific binding is prevented. See, e.g., Star et al., "Electronic Detection of Specific Protein Binding Using Nanotube FET Devices", *Nano Lett.*, vol. 3, no. 4, pp. 459-63 (2003).

Many methods are known for non-covalently functionalizing nanotubes. See, e.g., J. Kong et al., "Nanotube Molecular Wires as Chemical Sensors," Science, vol. 287, pp. 622-25 (Jan. 28, 2000); U.S. Pat. No. 6,528,020; and U.S. Pat. Appl. No. 2002/0172963 to Kelley et al., "DNA-Bridged Carbon Nanotube Arrays." For example, coating of a nanotube with PMMA (polymethylmethacrylate) has been shown to sensitize the nanotube to $NO_2$ gas, and gold decoration of a nanotube has been shown to sensitize it to the presence of a thiol vapor, see U.S. Pat. No. 6,528,020. In fact, since nanotubes retain similar properties to graphitic sheets, nearly any method suitable for non-covalently functionalizing graphite may be used to functionalize nanotubes.

3. Covalent Functionalization

The third type of sensor utilizes a nanofabric element in which a covalently derivatized nanotube surface allows any of the interactions above.

Nanotubes have been functionalized using covalent chemical bonding methods—e.g., involving diazonium salts. See J. L. Bahr et al., "Functionalization of Carbon Nanotubes by Electrochemical Reduction of Aryl Diazonium Salts: A Bucky Paper Electrode," *J. Am. Chem. Soc.*, vol. 123, no. 27, pp. 6536-42 (2001); J. L. Bahr et al., "Highly Functionalized Carbon Nanotubes Using in Situ Generated Diazonium Compounds," *Chem. Mater.*, vol. 13, no. 11, pp. 3823-24 (2001). Other workers have used solvent-free methods such as aniline in isoamyl nitrate. See, e.g., C. A. Dyke et al., "Solvent-Free Functionalization of Carbon Nanotubes," *J. Am. Chem. Soc.*, vol. 125, no. 5, pp. 1156-57 (2003). Still others have used oxidative processes to functionalize nanotubes in one-pot reactions, in which all reactions occur in a single reaction vessel. See, e.g., M. G. C. Kahn et al., "Solubilization of Oxidized Single-Walled Carbon Nanotubes in Organic and Aqueous Solvents through Organic Derivatization," *Nano Lett.*, vol. 2, no. 11, pp. 1215-18 (2002). Yet others have covalently bound peptide nucleic acid sequences to single-walled carbon nanotubes. See, e.g., K. A. Williams et al., "Carbon nanotubes with DNA Recognition," *Nature*, vol. 420, p. 761 (2002).

For example, Williams et al., supra, uses an approach to providing covalently functionalized nanotube nanofabrics in which the unique properties of a nanofabric are combined with the specific molecular-recognition features of DNA by coupling a nanofabric to peptide nucleic acid (PNA, an uncharged DNA analogue) and hybridizing these macromolecular wires with complementary DNA. This allows the incorporating of DNA-derivatized nanofabrics into larger electronic devices by recognition-based assembly, and allows using nanofabrics as probes in biological systems by sequence-specific attachment. The technique used to couple nanofabrics covalently to PNA involves ultrasonically shortening nanofabric ropes for 1 hour in a 3:1 mixture of concentrated $H_2SO_4$ and $HNO_3$. Subsequent exposure to 1 M HCl produces abundant carboxyl end-groups. This material is then dispersed in dimethylformamide (DMF, 99.5%) and incubated for 30 min in 2 mM 1-ethyl-3-(3-dimethylaminopropyl)carbodiimide hydrochloride and 5 mM N-hydroxysuccinimide (NHS) to form nanofabric-bearing NHS esters. PNA adducts are then formed by reacting this material in DMF for 1 hour with excess PNA (sequence: NH2-Glu-GT-GCTCATGGTG-CONH2, where Glu is a glutamate amino-acid residue and the central block represents nucleic-acid bases). The PNA-derivatized nanofabric is transferred to water and dispersed in 0.5% aqueous sodium dodecyl sulphate. To examine DNA hybridization to this modified nanofabric, fragments of double-stranded DNA with 12-base-pair, single-stranded "sticky" ends that were complementary to the PNA sequence were used. These fragments were produced by cutting double-stranded DNA with restriction enzymes and ligating the products to single-stranded oligonucleotides. This sticky DNA was hybridized to the PNA-nanofabric in water, deposited on freshly cleaved mica with 5 mM $MgCl_2$. The surface was rinsed and dried. Atomic-force micrographs of the DNA/PNA-nanofabric hybrids may then be recorded. The antisense properties of this derivatized complex may be exploited in biological applications, for example in biosensors.

These methods allow appreciable and measurable functionalization of nanotubes with specific moieties or sensing agents added directly through covalent bonding. In effect, the functionalized nanotube becomes a reactive chemical itself and further chemistry can be performed to yield such diverse species as nanotubes with nanocrystals and inorganic compounds. See, e.g., S. Banerjee et al., "Functionalization of Carbon Nanotubes with a Metal-Containing Molecular Complex," *Nano Lett.*, vol. 2, no. 1, pp. 49-53 (2002); S. Banerjee et al., "Synthesis and Characterization of Carbon Nanotube-Nanocrystal Heterostructures," *Nano Lett.*, vol. 2, no. 3, pp. 195-200 (2002); S. Banerjee et al., "Structural Characterization, Optical Properties, and Improved Solubility of Carbon Nanotubes Functionalized with Wilkinson's Catalyst," *J. Am. Chem. Soc.*, vol. 124, no. 30, pp. 849048 (2002). These functionalized-nanotube building blocks can be modified using the wealth of available chemistries to decorate them with groups and moieties necessary to sense nearly any chemical or biological agent desired.

As is the case with non-covalently functionalized, covalently functionalized nanotubes may be used in three ways to create nanosensors. The nanotubes may be functionalized separately and applied to a substrate, for example, by using a spin coating method or other method of application. In another embodiment, the nanofabric may be applied to a substrate and subsequently covalently functionalized before patterning. In yet another embodiment, the nanofabric may be functionalized after creation and patterning of the nanofabric. Each of these three methods lends itself to creation of a nanofabric comprising one or more types of functionalized nanotubes in the presence or absence of pristine nanotubes, depending upon the sensor application desired. Upon successful generation of a source of nanotubes containing the proper set of functional moieties, a nanosensor can be fabricated using various methods.

4. Hybrid

The fourth type of sensor uses a mixture of two or three of the previous types. By using such a mixture, a hybrid nanosensor is created with multiple binding-site types potentially able to detect multiple analytes and analyte types. Many different possible compositions of surface-functionalized nanotubes can be created before nanotubes are applied to the substrate, thereby allowing for a mixture of sensing components which can simultaneously screen for discrete analytes.

Methods of Making Exemplary Embodiments

FIGS. 4(A)-(L) collectively illustrate various intermediate structures created during an exemplary method for creating a substantially vertical nanosensor, including a nanosensor such as that of FIG. 3(A). The steps shown are for illustrative purposes. Similar techniques and steps can be used to create other nanosensor structures, including those of FIGS. 2(D) and 2(E).

Figure 4:
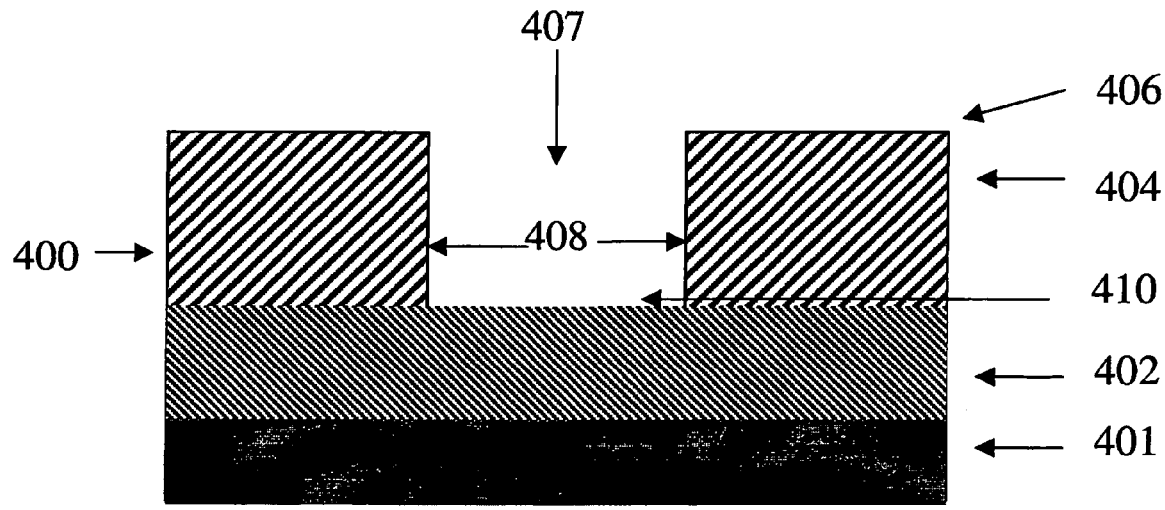
FIGS. 4(A)-(L) illustrate acts of making vertical nanosensor devices according to certain embodiments of the invention.
Figure 4:
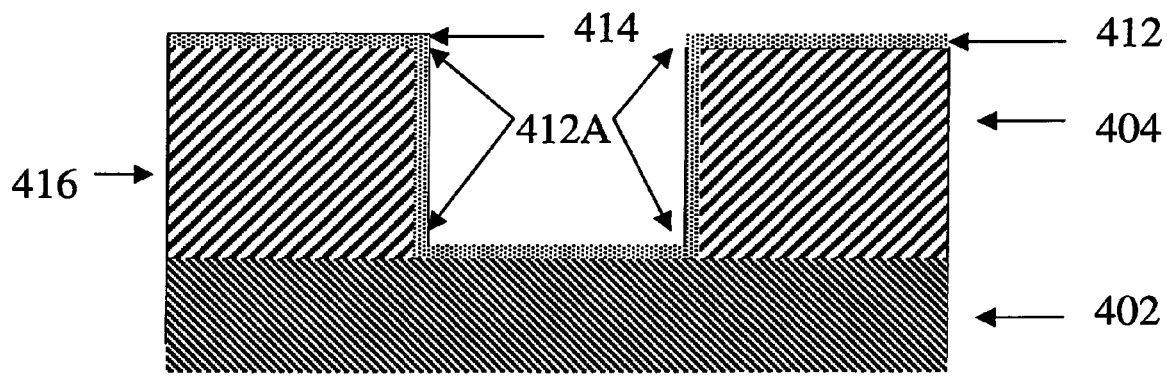
Figure 4:
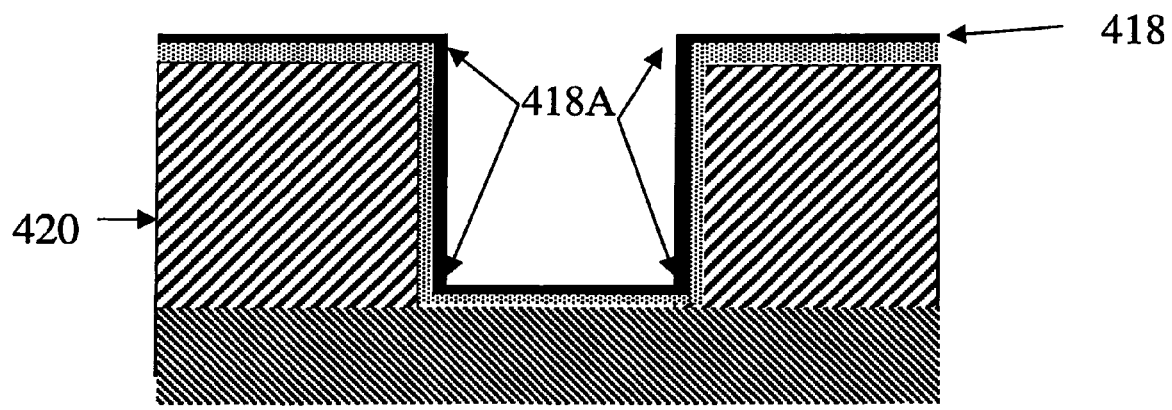
Figure 4:
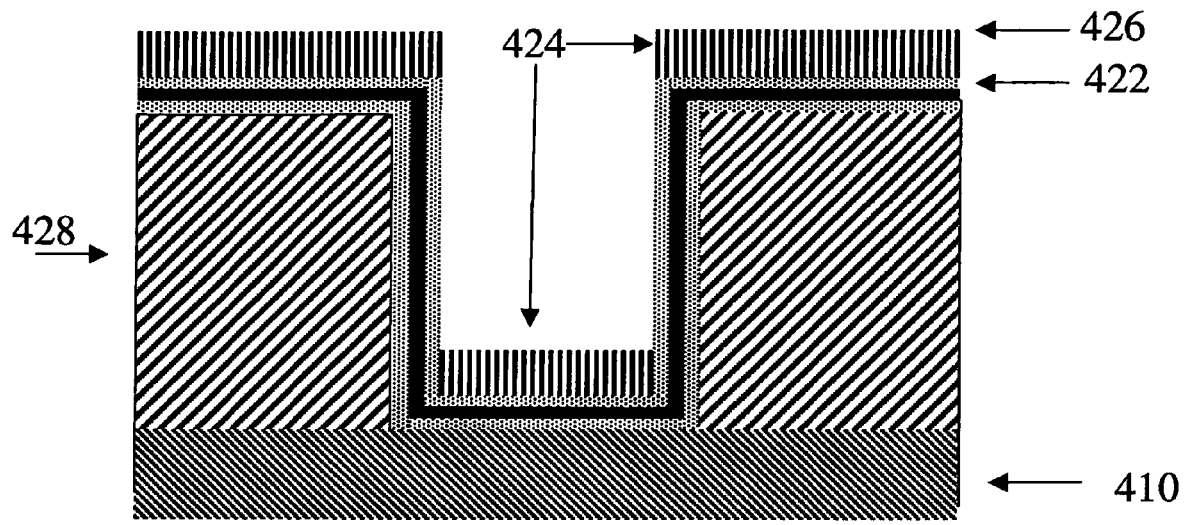
Figure 4:
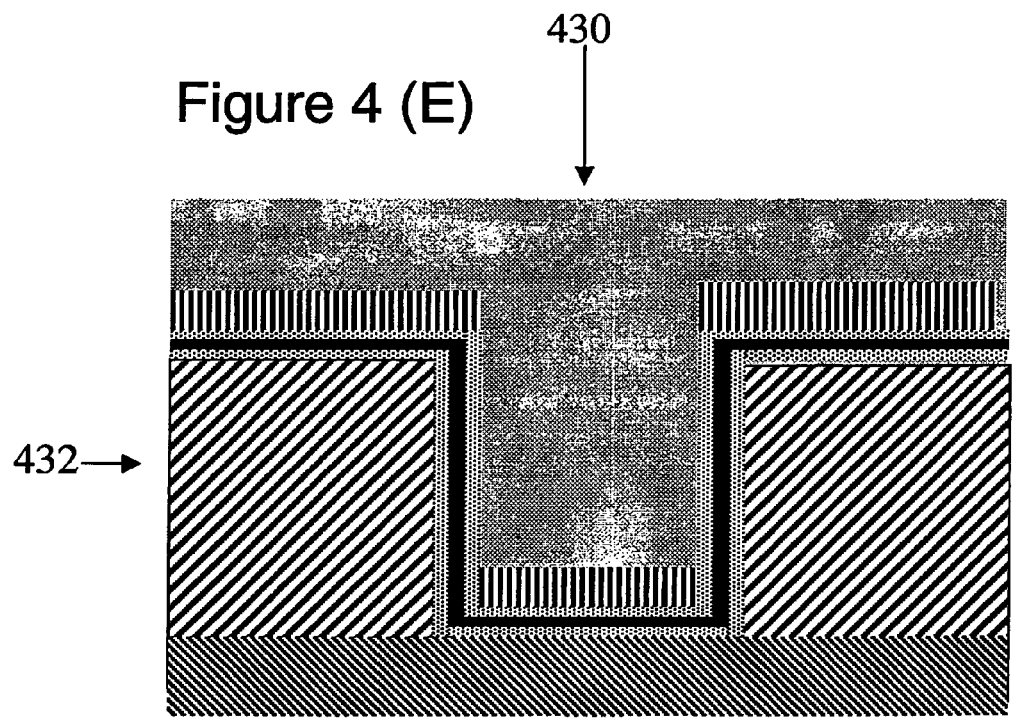
Figure 4:
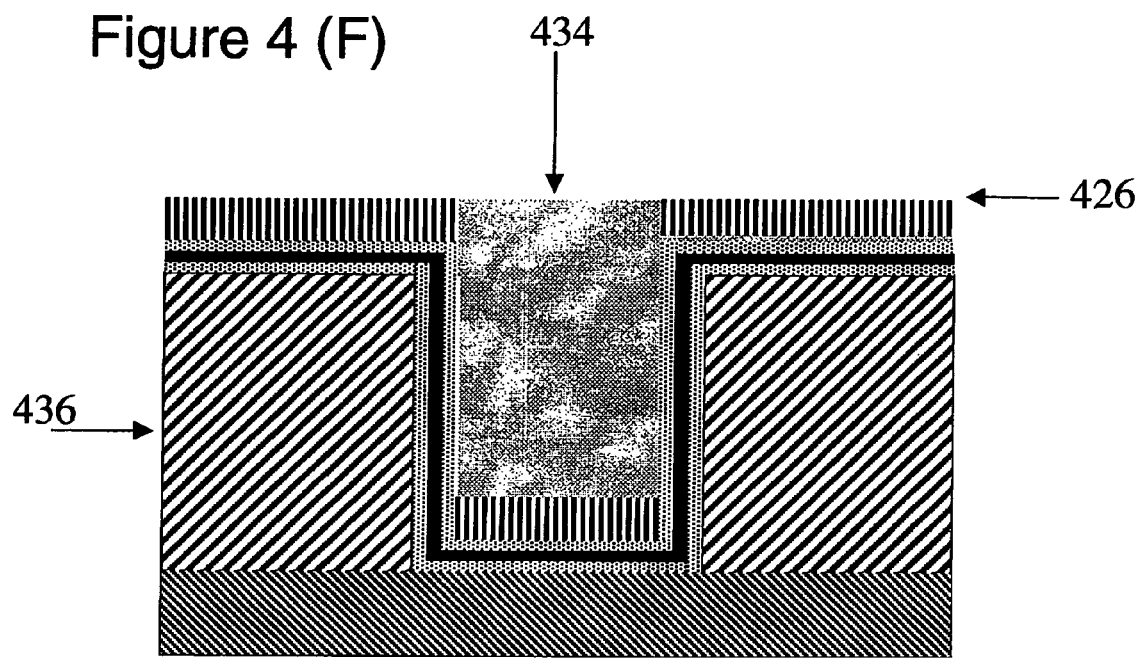
Figure 4:
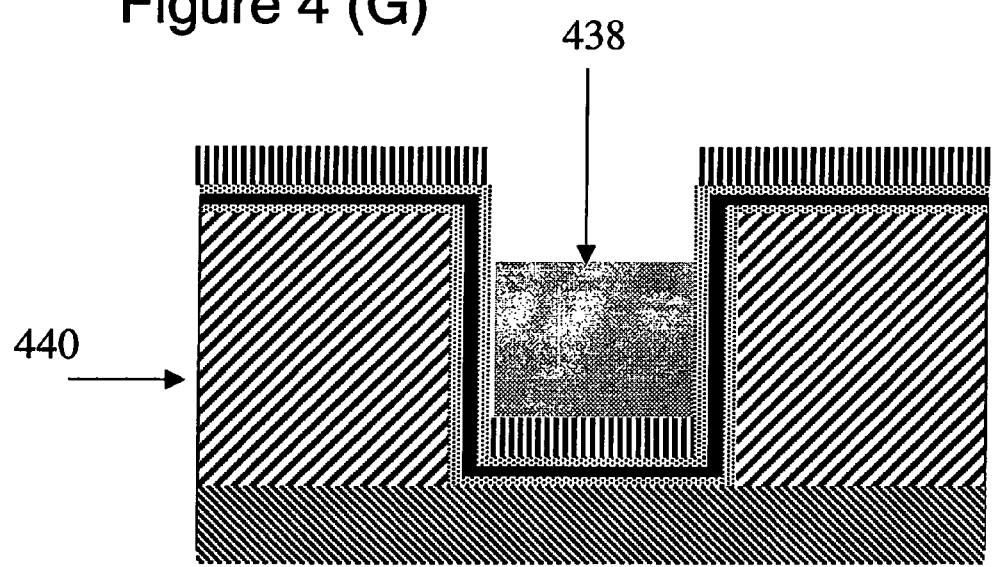
Figure 4:
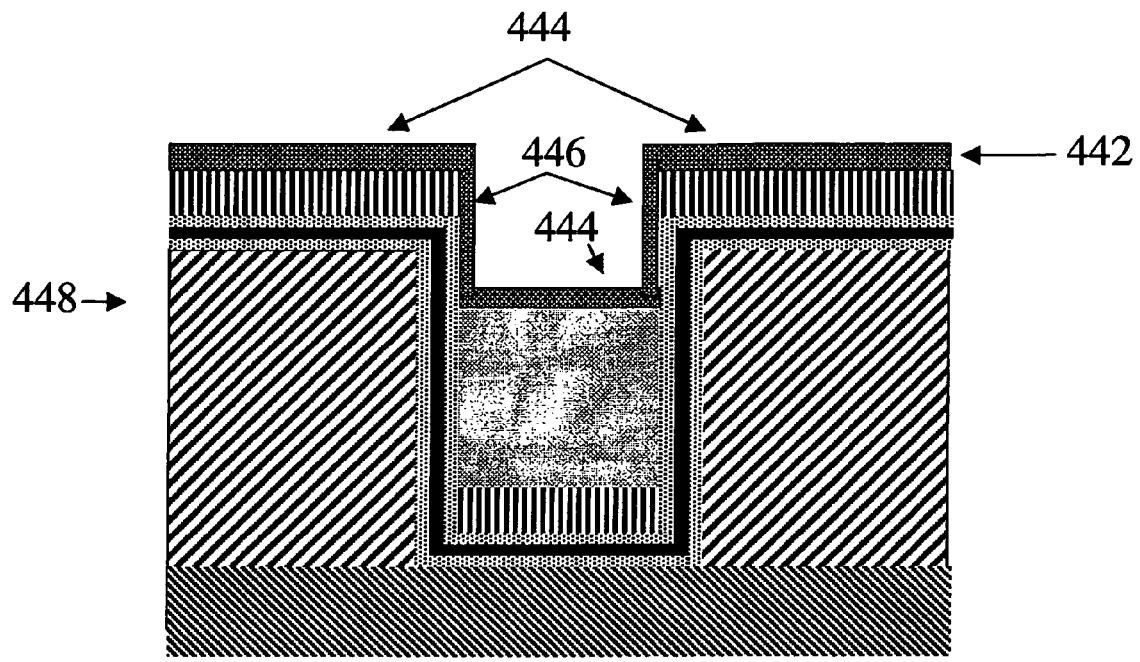
Figure 4:
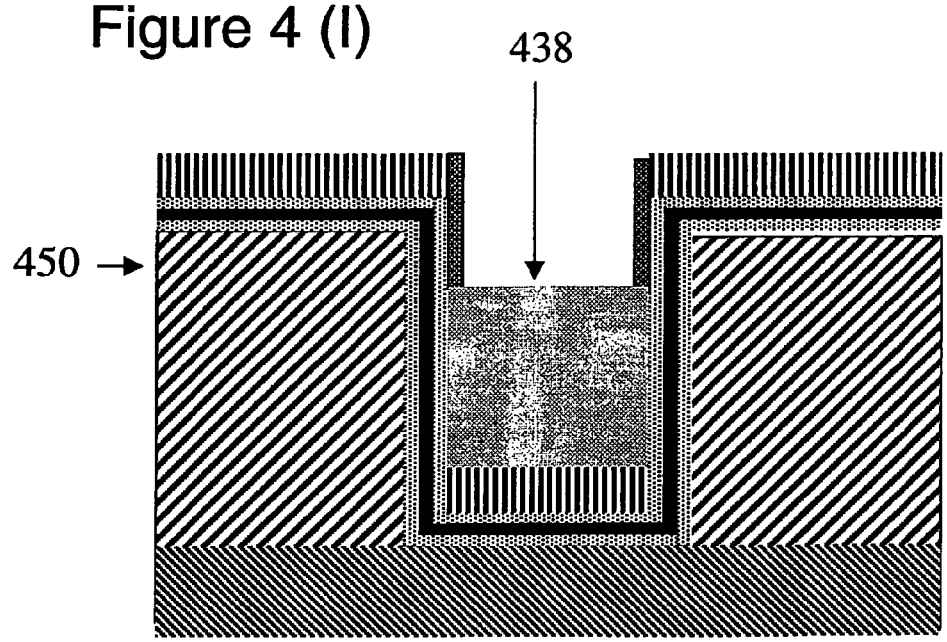
Figure 4:
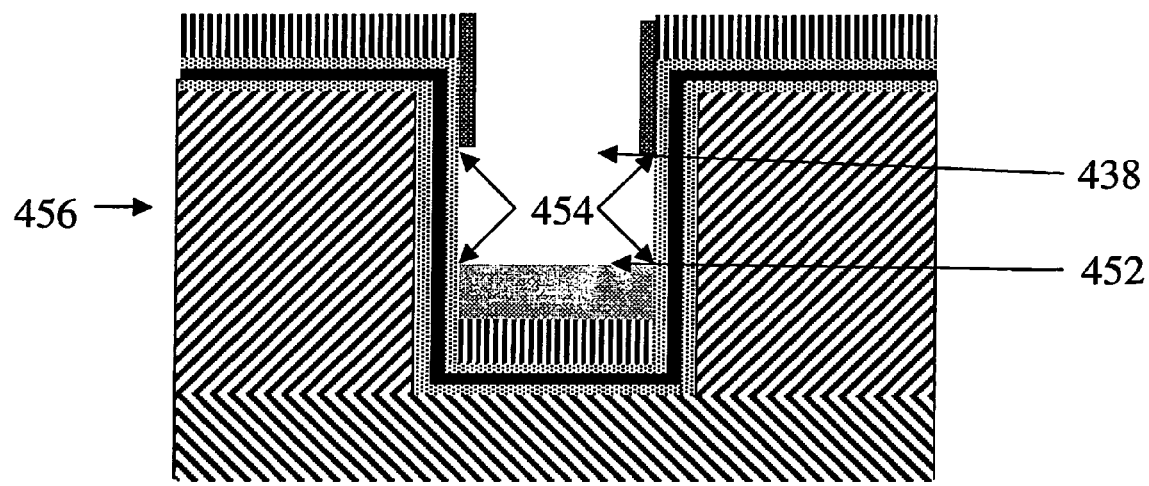
Figure 4:
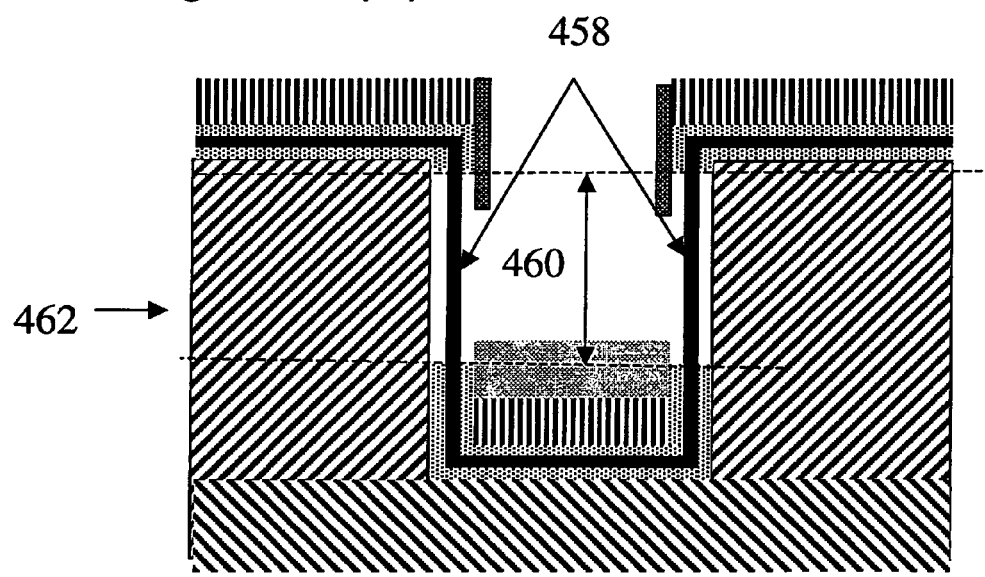
Figure 4:
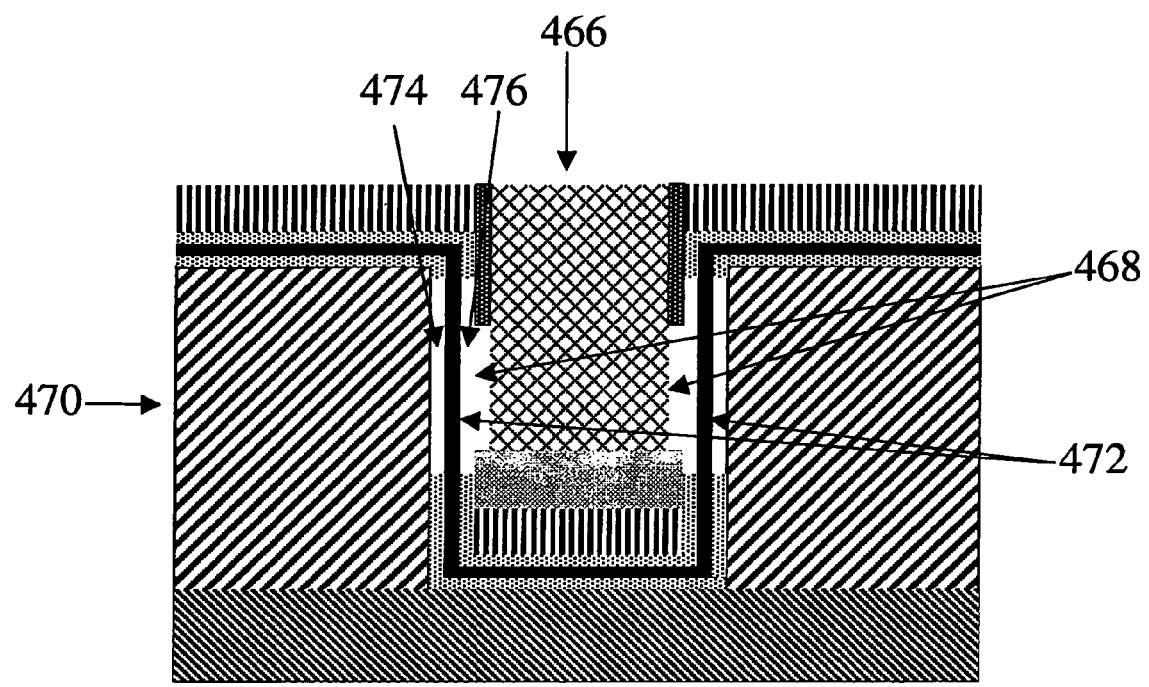

A silicon wafer substrate 400 with an insulating or oxide layer 402 is provided. Alternatively, the substrate may be made from any material suitable for use with lithographic etching and electronics, and the oxide layer can be any suitable insulator. The oxide layer 402 is preferably a few nanometers in thickness, but could be as much as 1 μm thick. A second layer 404 is deposited on insulating layer 402. The second layer has a top surface 406. Two non-exclusive examples of the material from which the second layer 404 can be made are metal or semiconductor. A cavity 407 is defined in the second layer 404. The cavity 407 can be created in the second layer 404 by reactive ion etching, and is defined by inner walls 408 and, in certain embodiments, an exposed top surface 410 of insulating layer 402 at the base of the cavity. In certain other embodiments, a portion of second layer 404 remains such that the bottom of the cavity 407 is conductive. (Alternatively, as illustrated by FIG. 4(B), an insulating layer 412 could be provided to top surface 406 which could then be etched to generate a cavity.) The cavity 407 can be prefabricated as part of a trench or a via provided as part of preprocessing steps—e.g., as part of an overall integration scheme in the generation of an electronic device.

A first insulating layer 412 made of silicon nitride or other material is deposited on top of the exposed top surface 410 and top surface 406 to generate top layer 414 of intermediate structure 416 in FIG. 4(B). According to one embodiment, the first insulating layer 412 is selectively etchable over polysilicon, nanotubes, silicon oxide, or another selected insulator. The first insulating layer 412 can act as a sacrificial layer to create a gap between subsequent layers and can be in a non-limiting range of thicknesses on the order of 100 to 200 nm.

Nanotube fabric 418 is applied to intermediate structure 416, forming intermediate structure 420 of FIG. 4(C). As described in references listed and incorporated above, non-limiting methods of applying such a fabric that may be used are chemical vapor deposition, spin coating, aerosol application, and dipping.

Like the nanofabric layer pictured in FIG. 1, nanofabric layer 418 conforms to the underlying insulating layer 412 and substantially follows the geometry of cavity 407. The resulting structure 420 thus includes two vertical portions 418A of the nanofabric 418, which portions are designed to be substantially perpendicular to a major surface of substrate 401.

A second insulating layer 422 is applied over nanofabric 418. Protective insulating layer 424, which may be an oxide layer, is deposited on top of second insulating layer 422 having top surface 426, to form intermediate structure 428 of FIG. 4(D). Deposition of protective insulating layer 424 on the sidewalls of the channel is substantially avoided. An exemplary but non-limiting thickness of protective insulating layer 424 can be on the order of 100 nm. The optimal thickness may be determined based on the need to protect the layers below protective layer 424 from additional etching or deposition steps. A non-exclusive example of the method of application of protective insulating layer 424 is sputtering or high-density plasma deposition of silicon dioxide.

A polysilicon layer 430 is deposited on top surface 426 of intermediate structure 428 of FIG. 4(D), filling the space between walls 408 in cavity 407 to give intermediate structure 432 of FIG. 4(E). Polysilicon layer 430 can be deposited to a height greater than that of top surface 426 in order to get at least the proper amount of polysilicon layer into cavity 407, creating an overfilling condition as in intermediate structure 432. Polysilicon layer 430 may be subsequently planarized to etched polysilicon layer 434 with top surface 426 of oxide layer 424, as illustrated by intermediate structure 436 of FIG. 4(F).

FIG. 4(G) illustrates etched polysilicon layer 434 etched to a first depth 438, by any appropriate method. An exemplary method of creating such a depth is by reactive ion etch ("RIE") and is shown in intermediate structure 440. First depth 438 later helps in the definition of one edge of a suspended nanofabric segment. The thickness of the etched polysilicon layer 434 depends, in part, on the depth of the original cavity 407, which, in certain embodiments, may be in a range from 200 nm to 1 micron. For certain applications requiring ultrahigh speed electromechanical switching sensors, this depth might preferably be below 200 nm. This depth can be reduced using thin film manufacturing techniques, as discussed below and in documents incorporated by reference.

A layer of oxide 442 is deposited on exposed surfaces of intermediate structure 440 to form intermediate structure 448 of FIG. 4(H). Vertical portions of oxide layer 446 cover trench walls, and horizontal portions of the oxide layer 444 cover top surfaces of polysilicon layer 434 and protective layer 424. Horizontal oxide layers 444 are removed—for example, by oxide spacer etching—leaving intermediate structure 450 of FIG. 4(I).

FIG. 4(J) illustrates polysilicon layer 434 etched to a second depth 452. Second depth 452 may be approximately 50 nm deeper than first depth 438. The defined gap 454 allows exposure of regions of second insulating layer 422, as shown in intermediate structure 456.

Since nanofabrics are permeable, the regions 412A of first insulating layer 412 (see FIG. 4(B)) that are adjacent to the regions of nanotube fabric 418A (see FIG. 4(C)) are removable—for example, by wet etching. Removal of materials from beneath a porous nanofabric has been described by the present applicants in incorporated references. Suitable wet etching conditions to remove regions of first insulating layer 412 and second insulating layer 422 leave a suspended nanofabric 458 having approximate vertical height 460 as observed in intermediate structure 462 of FIG. 4(K). The wet etching may leave an overhang owing to the nature of isotropic wet etching conditions. Other techniques such as dry etching may be utilized to provide an anisotropic etching step. Indeed, various methods of preparing the described structures exist and the inventors use the foregoing as examples to illustrate the versatility of such methods in providing a suitable nanofabric sensing structure.

Vertical height 460 is defined by the etching procedure. When vertical height 460 is about 200 nm, the thicknesses of first insulating layer 412 and second insulating layer 422 should preferably be approximately 20 nm if it is desired to have nanosensing elements have alternate nonvolatile "off" and "on" states. If insulating layer thicknesses to generate an air gap are instead approximately 50 nm, deflected states may instead be volatile.

Structure 462 of FIG. 4(K) may be viewed as "final" structure incorporating two nanosensing elements like that shown in FIG. 2(A). Alternatively, if first insulating layer 412 had been made of a material not removed by the process that removed portions of second insulating 422, the structure that would have resulted would incorporate nanosensing elements like those of FIG. 2(E).

On the other hand, if a three-trace structure or other structure of additional complexity is desired, additional steps are needed. For example, as indicated by FIG. 4(L), electrode material 466 may be deposited in trench 407, leaving gaps 468 between electrode material 466 and suspended nanotube fabric 458 as shown in intermediate structure 470. The resulting structure 470 has a pair of vertically suspended nanofabric portions 472 surrounded by vertical gaps 474 and 476 on either side of each vertically-suspended nanofabric portion 472.

Structure 470 thus incorporates two nanosensing elements like that of FIG. 3(A), and thus may serve as a basis for a pair of bi-state or tri-state switching sensors. (Bi-state cells may be fabricated with the same elements as tri-state cells, but, in bi-state cells, the gap distance between the nanofabric and one electrode should preferably be great enough to prevent nonvolatile contact, but close enough to be used to switch off an oppositely disposed nonvolatile sensor cell.) The behavior of such switching devices is influenced by the strain in the suspended nanofabric portions and the surrounding gap distances.

It is possible to implement many variations on the "common electrode" configuration of structure 470 (so-called because a single cavity electrode 466 interacts with both of the two nanosensing elements). For example, structure 470 can be split into discrete "left" and "right" sections by a divide running vertically through electrode 466, leaving bi- or tri-state switches that may be independently operated.

In these and other embodiments, the nature of the resulting devices and switches depends on the construction and arrangement of the electrodes and connections, among other factors. Attention is called to the construction of various types of electrodes in the following embodiments, as an indication of the flexibility of these devices and the variety of their potential uses. Some devices share common electrodes between more than one nanofabric article (e.g., two nanofabric switch elements being influenced by a same shared electrode). Other devices have separate electrodes that control the behavior of the nanofabric. One or more electrodes can be used with each nanofabric article to control the article, as discussed, for example, in the incorporated reference entitled "Electromechanical Three-Trace Junction Devices."

Figure 5:
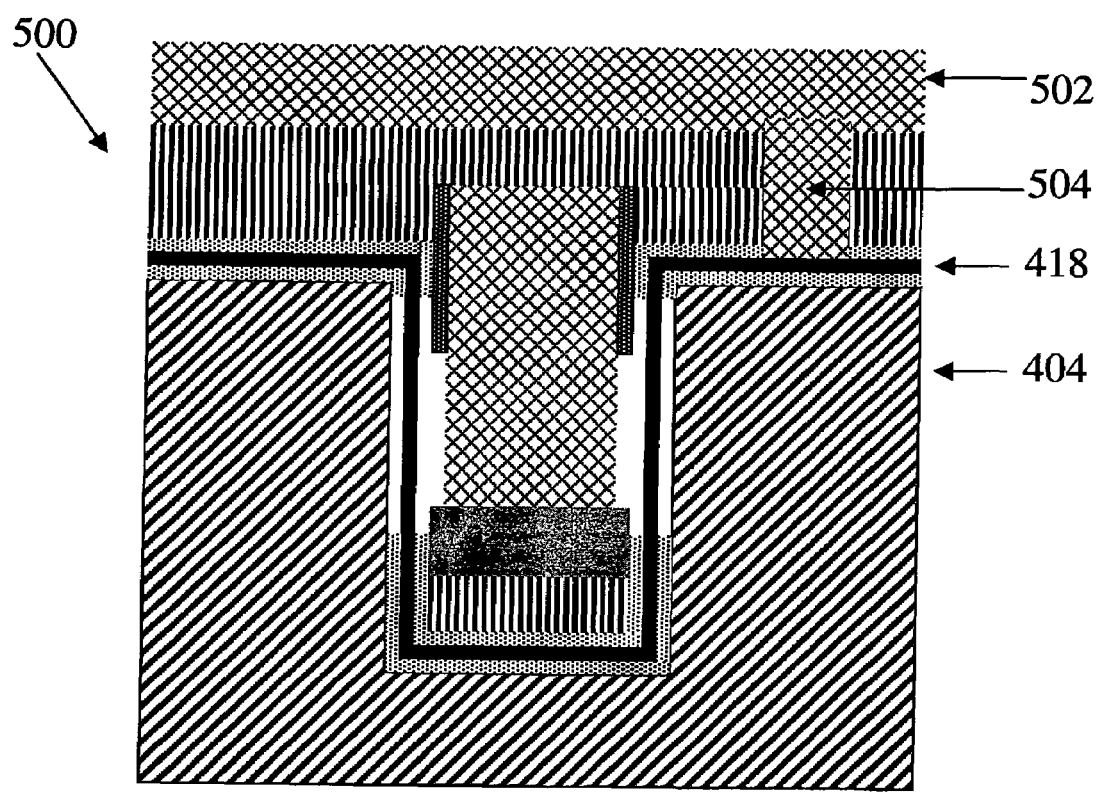
FIGS. 5-9 illustrate nanotube fabric sensor devices according to certain embodiments of the invention.

FIG. 5 illustrates an exemplary structure with subsequent layers of metallization. This structure 500 includes electrode interconnect 502 and via 504 in contact with nanofabric 418, and a contiguous metallic layer 404 surrounding the electromechanical switch both laterally and subjacently. It should be apparent to one skilled in the art that the nanofabric sensor is exposed to the milieu where it senses: although this may appear to be a closed structure, it is not necessarily so because areas surrounding the vertical nanosensor can be open to fluids of many types—for example, via open channels running through the three-dimensional structure (of which only a cross-section is shown in FIG. 5).

Figure 6:
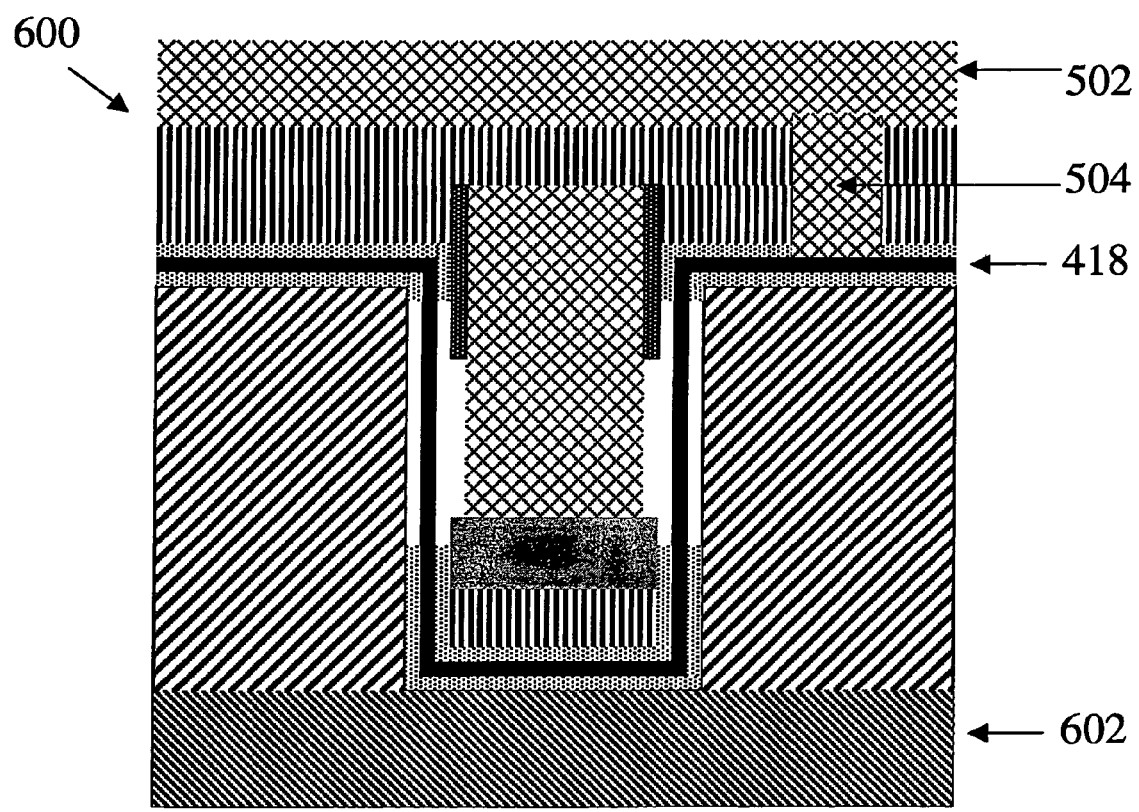

FIG. 6 illustrates another exemplary structure with subsequent layers of metallization. This structure 600 is similar to intermediate structure 500 in several respects. However, an insulating layer 602 separates the portions of metallic layer 404, and therefore metallic layer 404 does not surround the electromechanical sensor elements, substantially preventing crosstalk.

Figure 7:
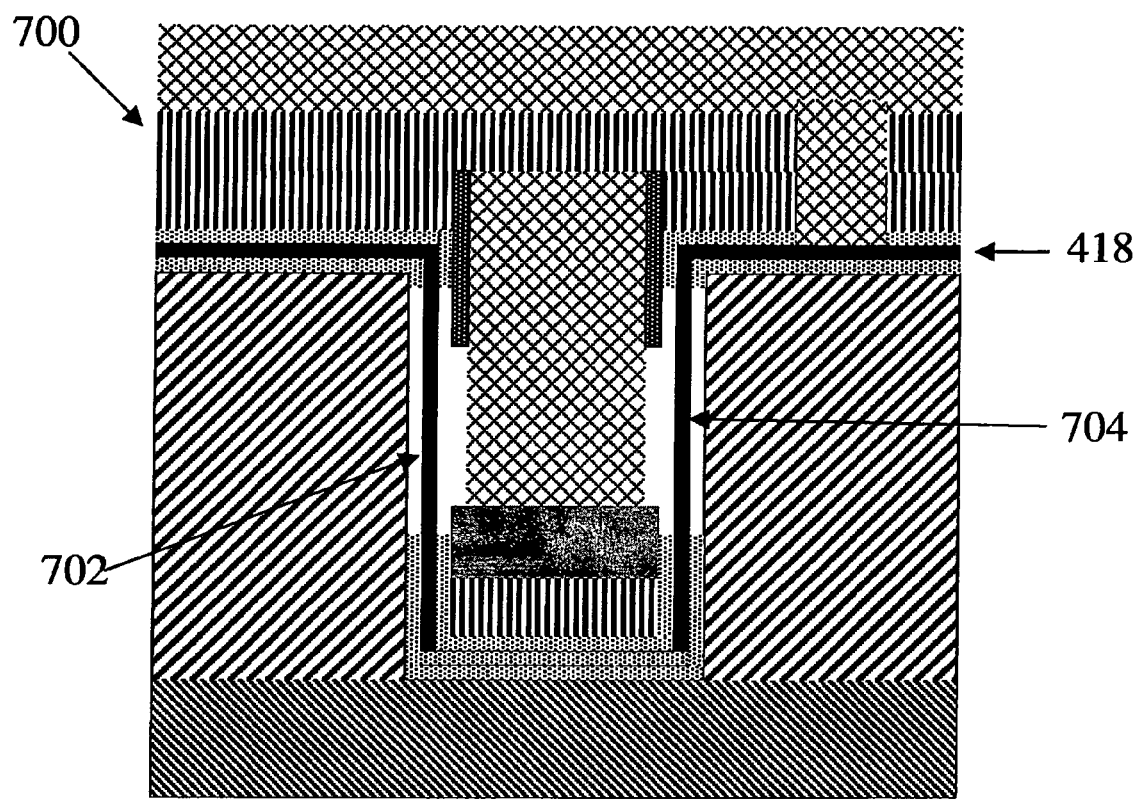

FIG. 7 illustrates another exemplary structure with subsequent layers of metallization. Structure 700 differs from structure 600 in that the nanofabric layer 418 is not continuous, and there are thus two independent sensors 702 and 704, which have substantially no crosstalk.

Figure 8:
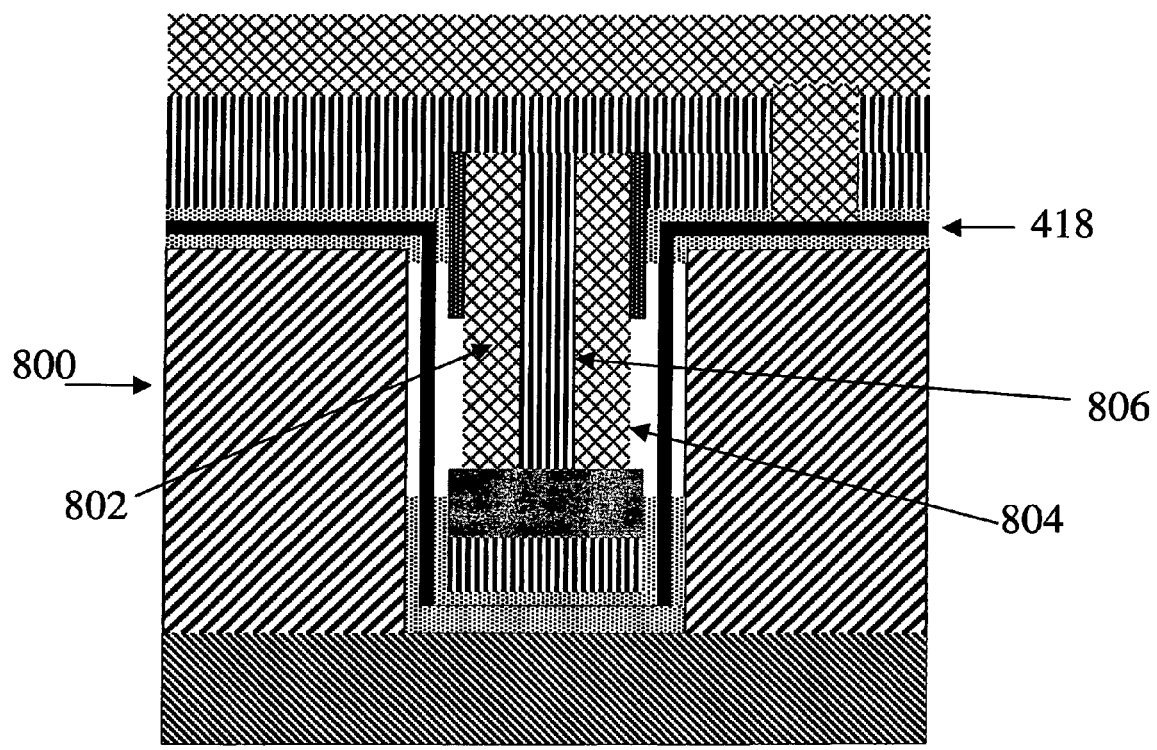

FIG. 8 also shows an exemplary structure with subsequent layers of metallization. Structure 800 differs from structure 700 in that, instead of a single central electrode, there are two central electrodes 802 and 804 separated by insulating layer 806. Intermediate structure 800 has two nanosensors, which can be operated or read substantially independently.

Figure 9:
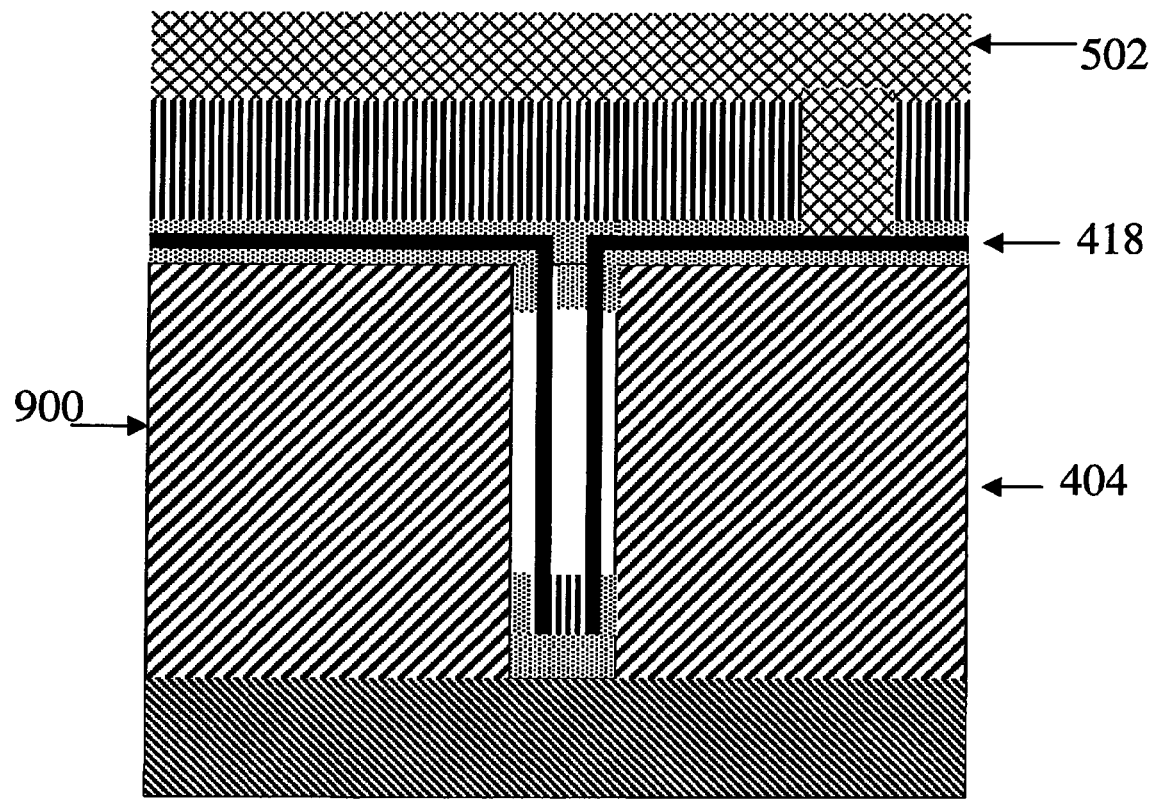

FIG. 9 displays an additional exemplary structure with subsequent layers of metallization. Structure 900 is similar to intermediate structures 700 and 800, except there is no central electrode at all. In this embodiment, it is possible for the nanofabric sensors to contact metallic layer 404 to make a volatile or nonvolatile switch, and it is possible for the switches to contact one another in a volatile or nonvolatile fashion, depending on further details of the design.

The devices and articles shown in the preceding embodiments are given for illustrative purposes only, and other techniques may be used to produce the same or equivalents thereof. Further, the design of the articles shown may be varied by substituting different types of materials and geometries, to make yet other embodiments. For example, rather than using metallic electrodes, some embodiments of the present invention may employ conductive interconnects made from nanotubes.

Use of additional electrodes can provide extra control of a switching sensor, non-switching sensor, or device constructed according to the present description. For example, FIGS. 3(A)-(C) show a device that has two distinct electrodes that can act together to push and/or pull a vertical nanofabric section. The gap distances help determine whether the devices are volatile or nonvolatile for a given set of parameters.

FIGS. 6 and 7 show devices having three distinct electrodes and thereby providing extra degrees of freedom (e.g., extra redundancy, extra information storage or sensing capability, etc.).

FIG. 8 shows four distinct electrodes, since the center electrode is divided into two electrodes 802 and 804 by application of divider 806.

On the other hand, FIG. 9 shows two electrodes located on opposite sides of the channel, and uses top electrode 502 as a third electrode, one having a direct electrical connection to nanofabric section 418.

There are other electrode connection locations and geometries possible that one skilled in the art would know to create.

Further details regarding one exemplary embodiment of a method for providing a nanofabric region in contact with electrodes able to be used for measurements or detection may be described as follows. Such a structure may be generated, in part, by using two standard photomasks to pattern gold contacts to a nanofabric line, which, for example, has dimensions of about 6 µm in length and 2 µm in width. The nanofabric contains pristine single-walled carbon nanotubes, and is treated with a mixture of 10 wt % polyethyleneglycol (PEG) with an average molecular weight of 25,000 and 10 wt % polyethyleneimine with an average molecular weight of 10,000 in water at room temperature overnight. The actual concentrations and amount of time required for this step can vary depending upon the size and density of the nanofabric required for the device. Also, it is noted that the nanotubes are exposed directly to solvent and must be handled with care in order to prevent damage to the nanofabric. For this reason, air drying rather than nitrogen blowing was performed. The nanotube fabrics could be allowed to dry in an oven with or without oxygen. After thorough rinsing in water, the nanofabric is subjected to a 15 mM solution of biotin-N-hydroxysuccinimide ester at room temperature overnight. After derivatizing of the free amine groups on the nanofabric overnight, the polymer-coated and biotinylated nanofabric can be tested for sensing capabilities by subjecting it to a 2.5 µM solution of streptavidin in 0.01 M phosphate buffered saline (pH 7.4) at room temperature. This test can be performed while electrical contacts are attached as long as the measurement voltage is sufficiently low. The electrical characteristics of the "pretested" (no streptavidin added) nanofabric are compared with those of the streptavidin-bound nanofabric to delineate a binding event.

The total concentration of binding moieties can be determined by using streptavidin that is bound with gold particles. The particles for a given area of nanofabric can be counted by SEM or AFM to determine the order of magnitude sensitivity available within a particular device. Since such derivatization can take place over an entire wafer, it is easy to generate nanofabric sensors with a very narrow range of characteristic binding concentrations (over 4 orders of magnitude or more).

The methods of fabrication for the nanotube sensors of certain embodiments of the present invention do not require the use of substrates that can withstand CVD temperatures. However, such substrates may also be used. The sensors of certain embodiments of the present invention are typically composed of nanotube fabrics that comprise redundant conducting nanotubes; these fabrics may be created via CVD, or by room-temperature operations as described herein and in incorporated references. In such a redundant sensor, if one sensing nanotube breaks, the device would remain operable because of the redundant conductive elements in each sensor. Because the nanosensor described herein can be fabricated at room temperature, the use of nearly any substrate, including highly flexible materials and plastics is possible.

Nanosensors according to certain embodiments of the present invention can be readily manufactured using standard techniques found in the semiconductor industry such as spin coating and photolithography. The feature size of each nanosensor can be determined by photolithography or by deposition. Because such standard techniques are used in the construction of the nanosensors, the overall cost, yield, and array size can be larger than sensors created by other known techniques. Nanosensor cells according to certain embodiments of the present invention can be used in massive parallel arrays and can be multiplexed using standard CMOS-compatible sense amplifiers and control logic.

The nanosensors according to certain embodiments of the present invention are compatible with high-resolution contact printing methods. See H. Li. et al., "High-resolution Printing with Dendrimers," *Nano Lett.*, vol. 2, no. 4, pp. 347-49 (2002). Patterned nanofabrics may be created on a substrate (as described below and in incorporated references), and those patterned nanotubes may be transferred via an appropriate contact printing method to a second substrate. Parameters such as solubility and binding affinity are important factors to be considered in selecting suitable substrates. Alternatively, functionalized, patterned nanotubes may be transferred in the same manner. And still another alternative that utilizes contract printing technology is the application of patterns of functionalization agent to specific, defined regions on patterned nanofabric—e.g., on different nanofabric sensor cells.

The inventors contemplate that standard semiconductor testing equipment can be used in conjunction with the nanofabric sensors in order to determine whether analytes are bound to nanofabrics. Examples of standard testing equipment include wafer probes.

Nanosensors according to certain embodiments of the present invention can be produced on surfaces that can withstand CVD temperatures and also on surfaces that may not withstand such a harsh environment—e.g., when spin coating or aerosol application methods are used to create the nanofabric.

As stated above, the nanotubes of the nanofabric may be derivatized or functionalized prior to formation of the nanofabric, subsequent to the formation of the fabric, or subsequent to the patterning of the fabric. In the latter case, for example, the three-dimensional structure might not be completely sealed but might instead have open channels whereby the nanofabric could be subjected to a derivatizing or functionalizing agent.

Note that the electrodes—for example, electrodes 466 and 404 of certain illustrated embodiments of the invention—may themselves be formed of nanofabric materials. In some embodiments, having a nanofabric ribbon or other nanofabric article in place of a metallic electrode permits removal of sacrificial materials from regions beneath or next to the electrode. Fluid may flow through a nanofabric material disposed above or adjacent to a sacrificial layer to remove the sacrificial material.

The devices and articles shown and described in the preceding embodiments are given for illustrative purposes only, and other techniques may be used to produce the same or equivalents thereof. Furthermore, the articles shown may be modified by the substitution of other types of materials or the use of different dimensions or geometries. For example, as described above, rather than using metallic electrodes, some embodiments of the present invention may employ conductive interconnects made from, or comprising, nanotubes. Moreover, using vertically oriented nanofabric articles permits exploitation of the smaller dimensions achievable with thin film technology, as opposed to those achievable with the lithographic techniques typically used for horizontally oriented nanofabric articles. For example, in a structure such as that depicted in FIG. 2(A), the electrode 208 may be formed using thin film techniques, and the dimension T across which nanofabric may be suspended—in this case, essentially the same as the thickness of the electrode 208—may be as little as a few nm thick (e.g., 10-100 nm, or less than 10 nm as technology develops). Gap distances such as distance 202 of FIG. 2(A) can similarly scale downward with the development of thin film technology. Consequently, a vertically oriented nanofabric sensor created by thin film deposition can be much shorter in length than horizontally oriented nanofabric devices, such as those in incorporated references.

In order to deliver samples to be examined by the sensor, a microfluidic delivery system may be utilized. Samples of blood, body fluids, chemicals, and the like may be injected or fed into a microfluidic delivery system. Such a system could then move material through a system of microfluidic capillaries and pumps to the sensor site. See, e.g., PCT publication WO 00/62931, "The Use of Microfluidic systems in the Electrochemical Detection of Target Analytes".

Figure 10:
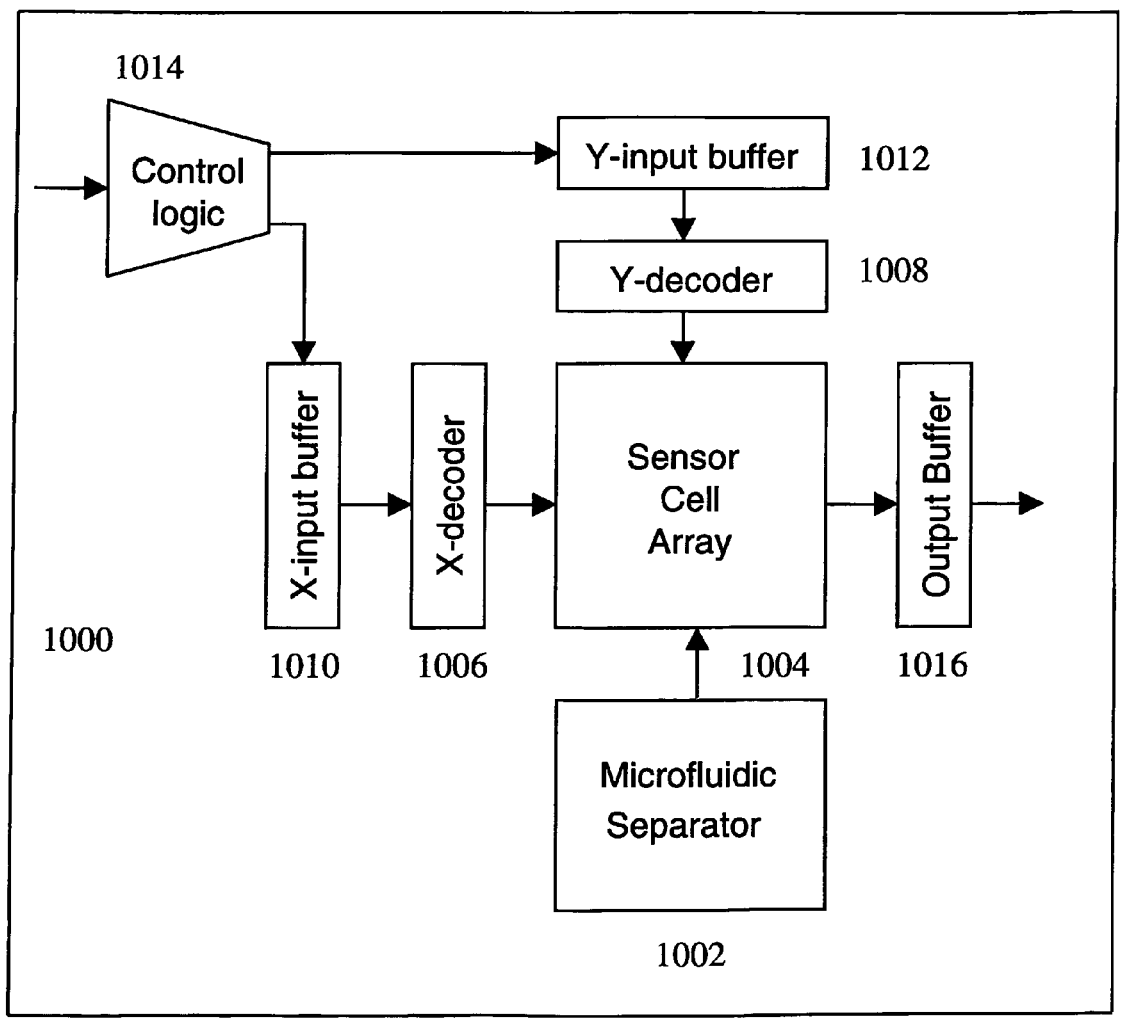
FIGS. 10 and 11 illustrate hybrid technology embodiments of the invention in which nanosensor arrays use nanotube technology and standard addressing logic.

Certain embodiments of the invention provide a hybrid technology circuit 1000, as shown in FIG. 10. A core nanosensor cell array 1004 is constructed using nanofabric as outlined above, and that core is surrounded by semiconductor circuits forming X and Y address decoders 1006 and 1008, X and Y buffers 1010 and 1012, control logic 1014, and output buffer 1016. The control circuitry surrounding the nanosensing core may be used for conventional interfacing functions, including providing read currents and sensing output voltages at appropriate times. Other embodiments may include various forms of logic to analyze the outputs at appropriate times.

In certain embodiments, the hybrid circuit 1000 may be formed by using a nanotube core (having either just nanosensor cells or nanosensor cells and addressing logic) and by implementing the surrounding circuitry using a field-programmable gate array.

Figure 11:
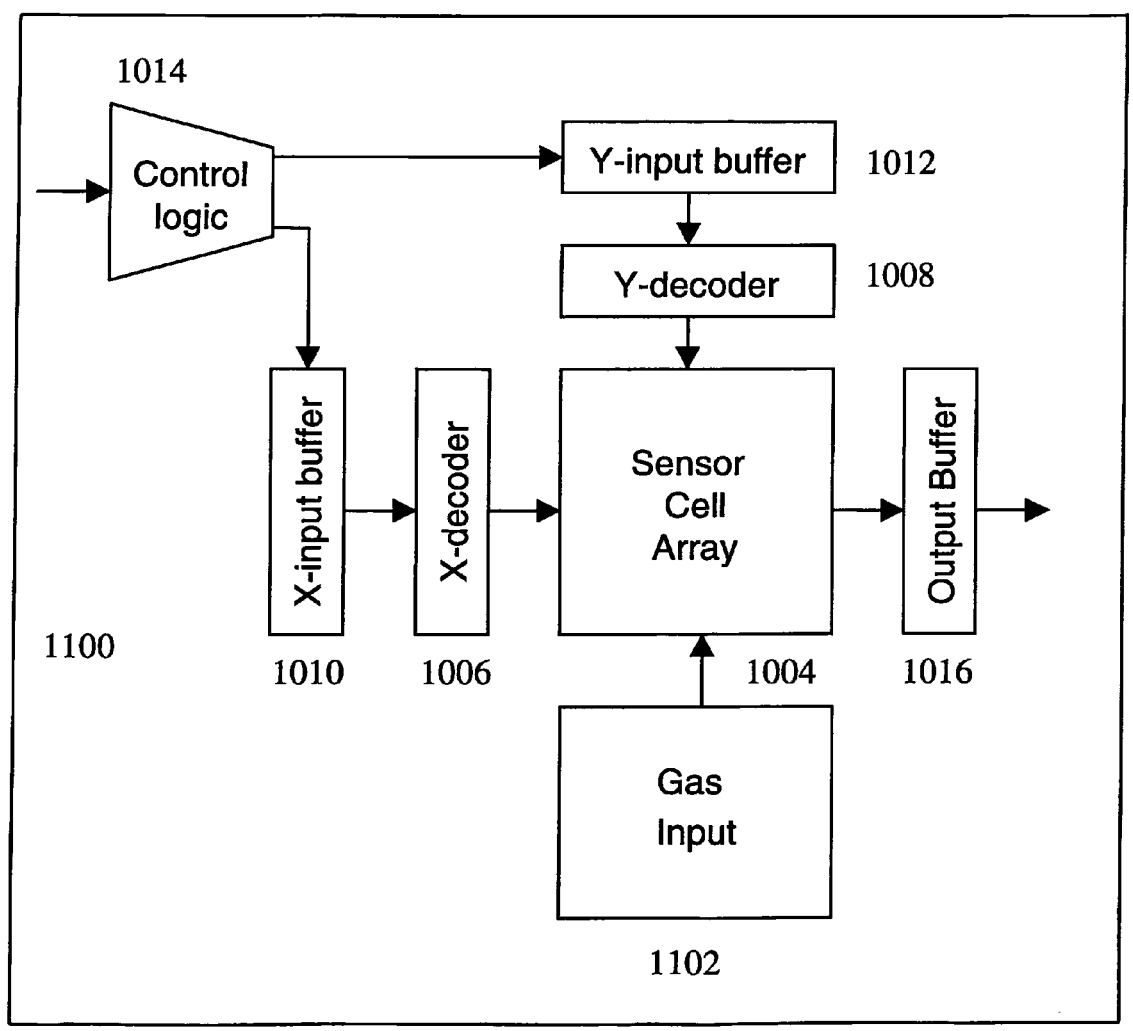

In another aspect of certain embodiments of the present invention, analogous to the structure shown in FIG. 10, a gas input means 1102 is utilized in place of the microfluidic separator 1002, as shown in structure 1100 of FIG. 11.

Figure 14:
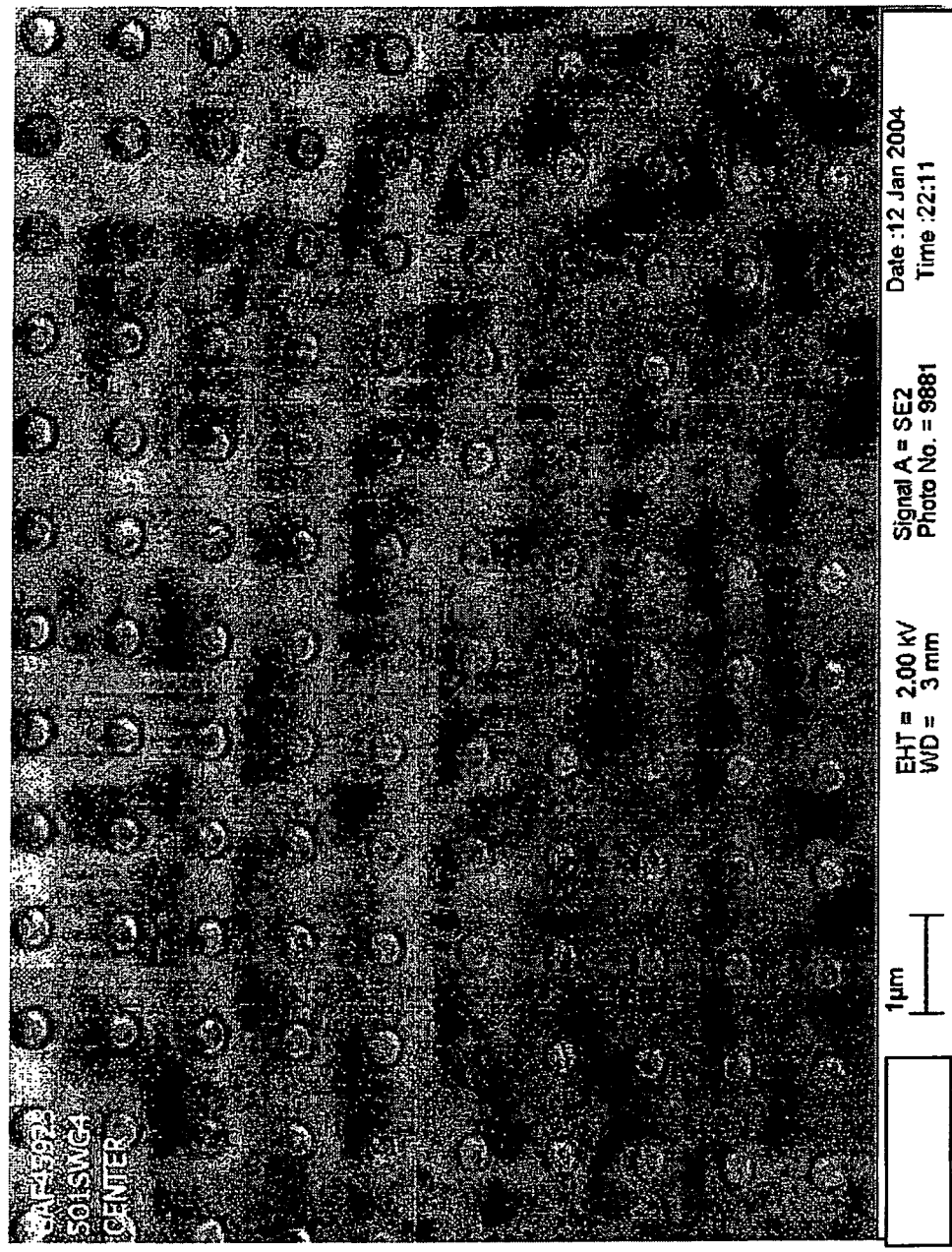
FIG. 14 is a scanning electron micrograph of an array of contact holes, in each of which a sensor element could be located to form a large-scale sensor array.

Some of the advantages of the sensors according to certain embodiments of the present invention include an ability to implement large scale application and integration. In addition, one circuit chip may be used for the sensors and for processing of the information from the sensors and for control of the sensors. This is facilitated by having CMOS-compatible manufacturing processes. FIG. 14 illustrates the possibilities for a large-scale array of addressable sensor elements by showing an array of contact holes in which sensor elements might be located.

Certain embodiments provide methods for detecting changes in electrical properties such as nanosensor capacitance or resistance through use of a current mirror sensing approach, see, e.g., Baker et al., *CMOS Circuit Design, Layout, and Simulation*, pp. 427-33 (1998). Investigators have shown that electrochemical properties of nanotube bundles and single carbon nanotube electrodes are reliable enough that such bundles and individual tubes can be used as electrodes in capacitors, see J. H. Chen et al., "Electrochemistry of Carbon Nanotubes and their Applications in Batteries and Supercapacitors," Electrochem. Soc., Proc., vol. 11, p. 362 (2001); Y. Tu et al., "Nanoelectrode Arrays Based on Low Site Density Aligned Carbon Nanotubes," *Nano Lett.*, vol. 3, pp. 107-09 (2003); and the present inventors have shown that electrical properties of single nanotubes are significantly maintained in nanofabrics (see references incorporated by reference).

As explained in the incorporated reference "Sensor Platform Using a Horizontally Oriented Nanotube Element" (U.S. patent application Ser. No. 10/844,913), filed on May 12, 2004, sensor cells may be constructed in which nanotube sensor elements are arranged in a capacitive relationship with one or more other conductive structures, and the structures and approaches to making such structures described therein can be readily extended to the vertically oriented sensors and methods for providing them described herein. For example, material comprising nanotube fabric may be arranged so that it is on one side of an insulating layer (e.g., an $Si_3N_4$ film), with a conductive pad being on the opposite side of the insulating layer. In such a formation, the nanotube-fabric material can act as one plate of a capacitor, the conductive pad can act as another plate, and the insulating layer can act as an intervening dielectric layer. Electrical connections and circuitry may then be provided to allow detection of the associated capacitance—for example, before and after exposure to a fluid (gas or liquid) that may carry a capacitance-altering analyte. Alternatively, the material comprising nanotube fabric might be protected from exposure by covering the side opposite the dielectric layer with a second insulating layer. The resulting capacitive structure could then be used to provide a reference capacitance, against which the capacitance of an analyte-sensitive capacitive structure could be measured.

Similarly, the application "Sensor Platform Using a Horizontally Oriented Nanotube Element" (U.S. patent application Ser. No. 10/844,913), filed on May 12, 2004, explains how a sensor cell may be constructed so that an associated resistance may be measured, and the structures and approaches to making such structures described therein can be readily extended to the vertically oriented sensors and methods for providing them described herein. Such a resistance cell may be constructed, for example, by including electrical contacts at two or more different places on a nanofabric layer. Further electrical connections and circuitry may then be used to measure the resistance encountered when current runs through the nanofabric between two of the contacts. A "reference resistor" might be constructed by encapsulating the nanofabric within one or more protective insulating layers. Alternatively, the nanofabric cell could be exposed so that its measured resistance—and, more particularly, changes therein—might be an indicator of the presence or passage of an analyte or an analyte-carrying fluid.

Figure 12A:
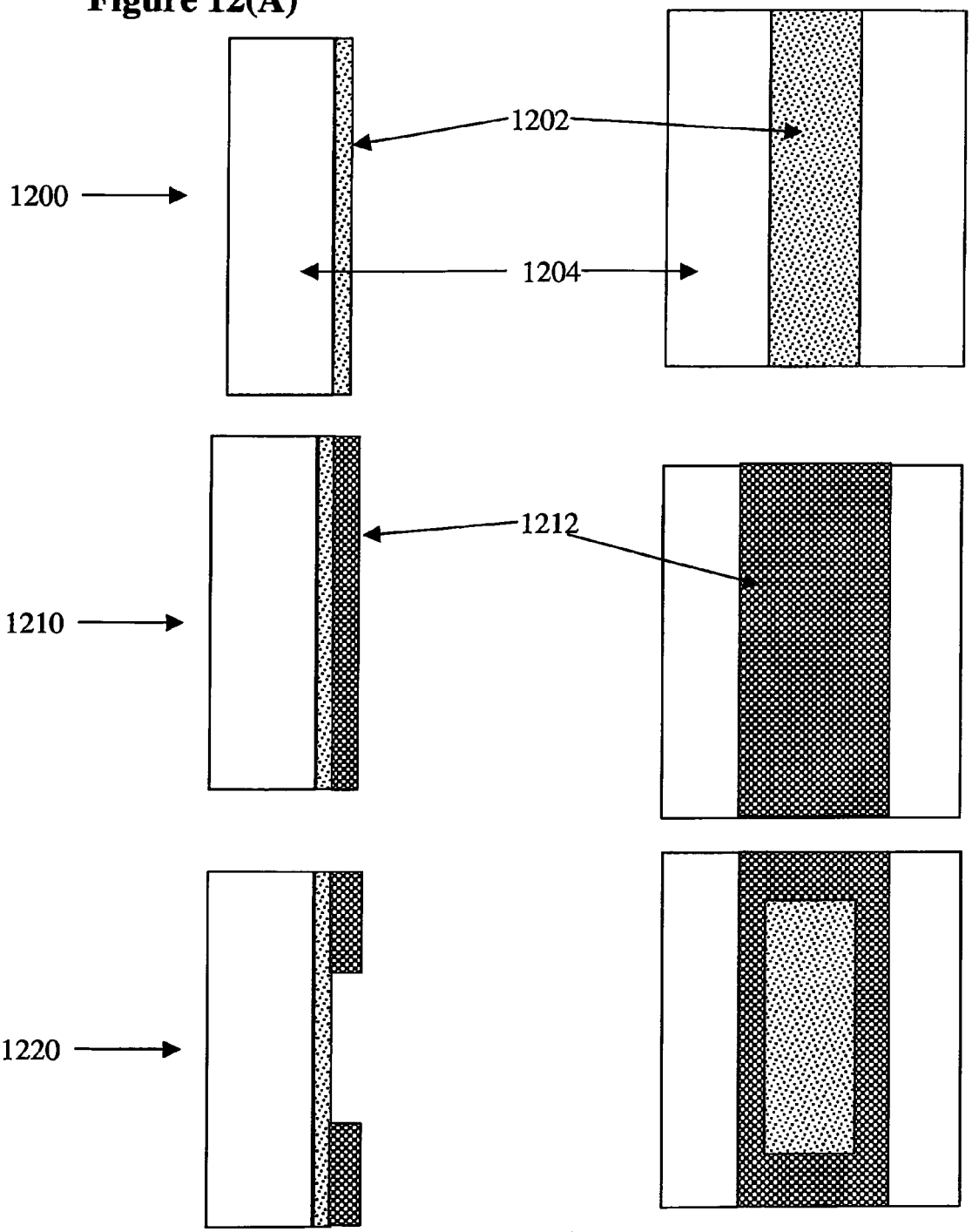
FIGS. 12(A)-(B) and 13 illustrate framed or patterned sensing-fabric structures and methods to create them.
Figure 12B:
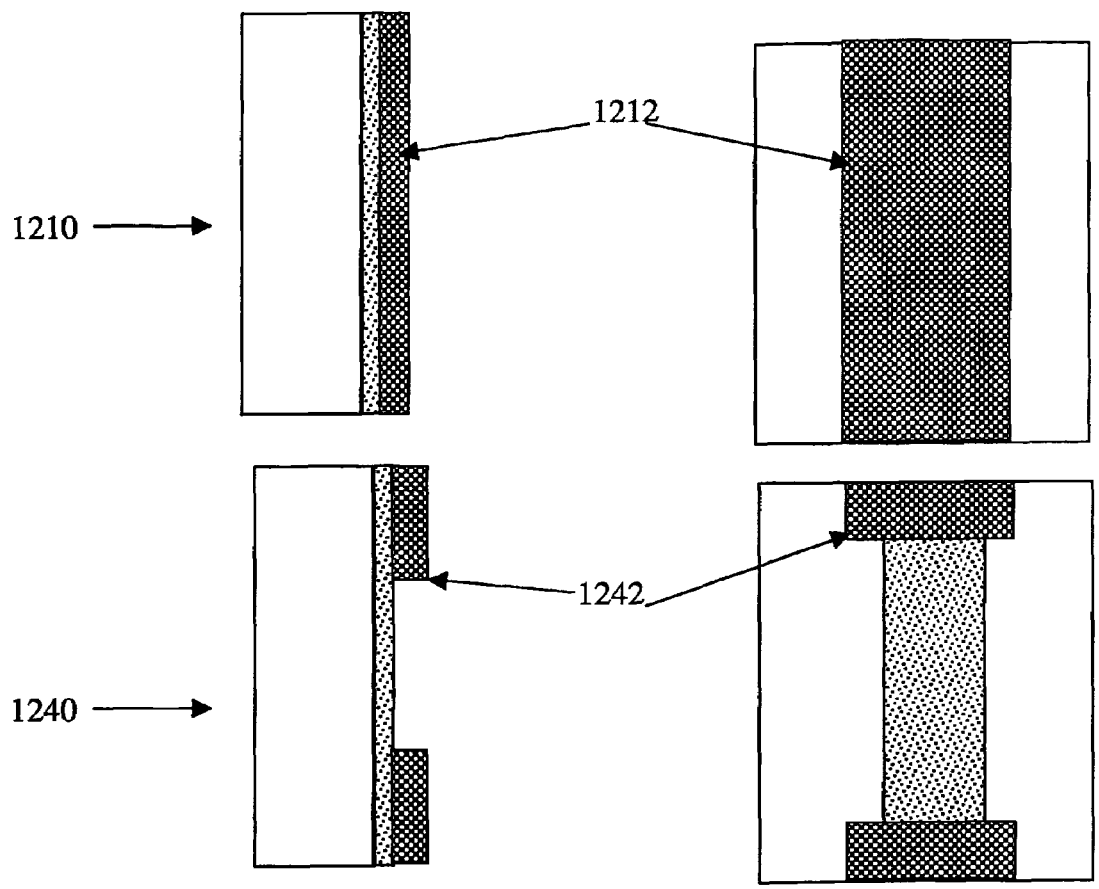
Figure 13:
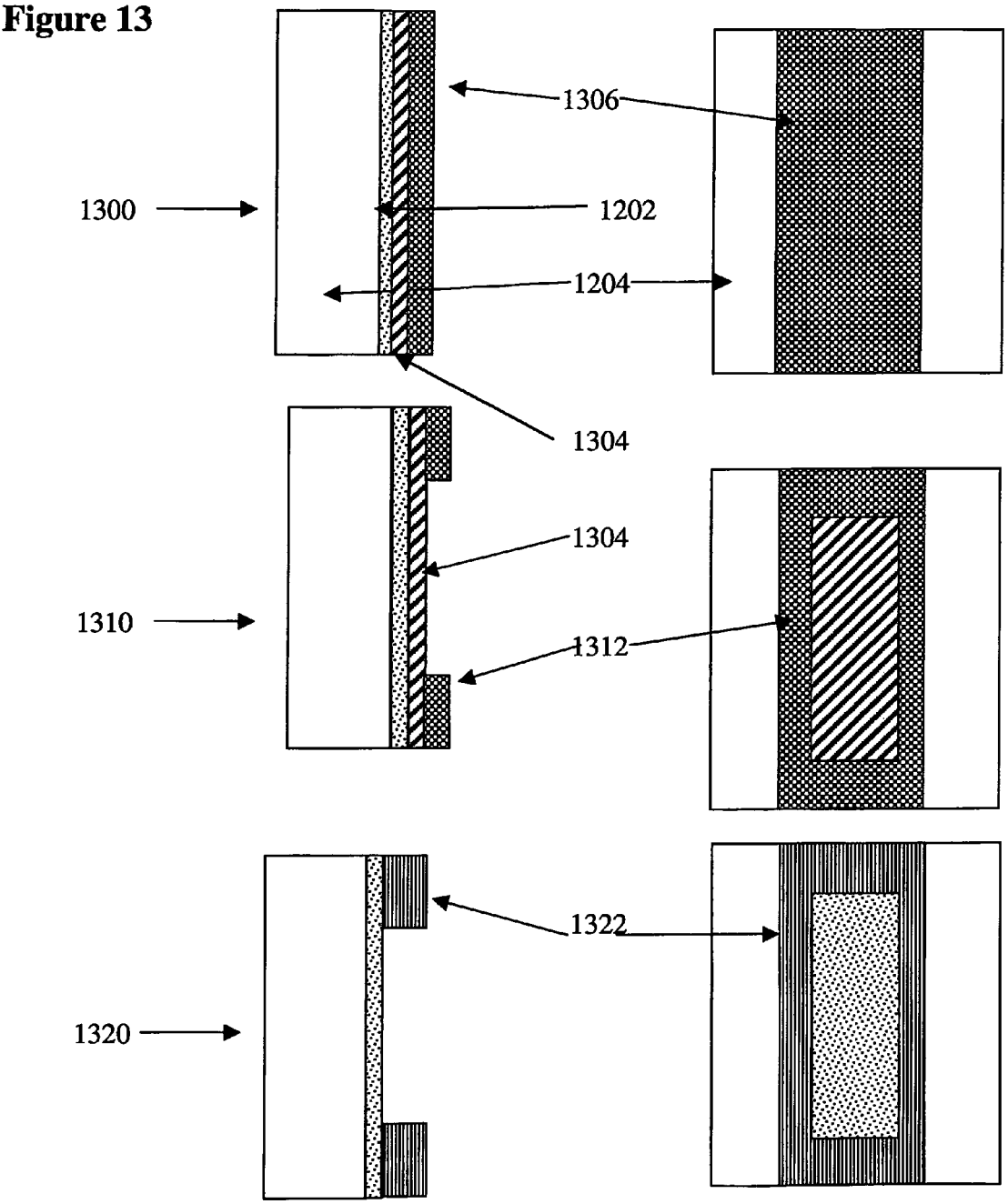

Furthermore, techniques like those illustrated in FIGS. 4(A) through 4(L) can be used to form framing or partial-covering layers for sensor elements, like those depicted in FIGS. 12(A) and 12(B). Likewise, a combination of covering layers can be used, in combination with a series of etching and annealing steps, to create a conducting composite layer that frames a sensor element, as illustrated in FIG. 13 and as described more fully in an analogous context in the incorporated reference, "Sensor Platform Using a Horizontally Oriented Nanotube Element" (U.S. patent application Ser. No. 10/844,913), filed on May 12, 2004.

OTHER EMBODIMENTS

Besides carbon nanotubes, other materials with electronic and mechanical properties suitable for electromechanical switching could be envisioned. These materials would have properties similar to carbon nanotubes but with different and likely reduced tensile strength. For embodiments designed to use or to enable electromechanical switching, the tensile strain and adhesion energies of the material used in place of carbon nanotubes must fall within a range for bistability of the junction and electromechanical switching properties within acceptable tolerances.

As one example of a use of materials other than carbon nanotubes, it may be noted that the fabric of a nanosensing capacitor may be made entirely of carbon nanotubes, or it may be made from nanowires of various composition—e.g., silicon nanowires—or the fabric may be a composite of nanotubes and nanowires. The creation of such nanowire and composite fabrics is more fully described in incorporated references such as U.S. provisional patent applications entitled "Patterning of Nanoscopic Articles."

Fluid samples delivered to a sensor element for analyte detection can include both liquids and gases, and may include analytes in a variety of forms—for example, as part of particulate matter suspended in a fluid.

Further, certain of the above aspects, such as the hybrid circuits and the nanotube technology for addressing, are applicable to individual nanotubes (e.g., using directed growth techniques, etc.) or to nanotube ribbons. As used herein, phrases such as "collection of at least one nanotube" or "collection of one or more nanotubes" each generally encompass a number of one or more nanotubes, and potentially other matter, without regard to such considerations as whether any particular constituent or constituents of the collection have a special quality or distinctiveness, or are arranged in a particular way.

A nanofabric sensor may be used as an electrode in a capacitor. Investigators have shown that electrochemical properties of nanotube bundles and single carbon nanotube electrodes are reliable enough that such bundles and individual tubes can be used as electrodes in capacitors. See J. H. Chen et al., "Electrochemistry of Carbon Nanotubes and their Applications in Batteries and Supercapacitors," *Electrochem. Soc., Proc.*, vol. 11, p. 362 (2001); Y. Tu et al., "Nanoelectrode Arrays Based on Low Site Density Aligned Carbon Nanotubes," *Nano Lett.*, vol. 3, no. 1, pp. 107-09 (2003). The present inventors have shown that electrical properties of single nanotubes are significantly maintained in nanofabrics (see incorporated references). It is therefore an object of certain embodiments of the present invention to use nanofabric as an electrode in a capacitor for use as a nanosensor.

The gaps of a porous nanofabric are especially helpful when capacitance differences are measured, because nanofabric/bound-analyte complexes exhibit different capacitances than the fabric sensor alone, and the capacitance difference is due in part to the greater surface are of the nanofabric alone, as opposed to the nanofabric with bound analytes.

The term "functionalization," as used herein, generally includes both covalent and non-covalent modifications of nanotubes whereas the term "derivatization" signifies the covalent modification of nanotubes. Hence, functionalization may in certain instances involve non-covalent transformation of the surface of a nanotube into a form with different functional groups or moieties, and, for example, is meant to encompass any alteration or addition to a nanotube or nanotube surface—including covalent derivatization—that creates a product with different physical or electrical characteristics. Derivatization is indicative of a covalent alteration of the chemical structure of one or more nanotubes, or a portion thereof. In both circumstances, the process can be controlled such that electrical properties of nanotubes may be substantially retained. Functional groups can include inorganic atoms and molecules as well as organic molecules. Significant biological functional groups include peptides, nucleic acids, antigens (including polypeptide and non-polypeptide antigens) as well as peptide nucleic acids.

It will be further appreciated that the scope of the present invention is not limited to the above-described embodiments but rather is defined by the appended claims, and that these claims will encompass modifications of and improvements to what has been described.

What is claimed is:

1. An electrical device, comprising:
a flexible substrate having a major surface and a second surface substantially non-parallel to said major surface;
a conductive article oriented disposed on said second surface of the substrate, said article comprising a non-woven fabric of nanotubes for providing a plurality of conductive pathways along the article; and
an electrode in electrical communication with at least a portion of the conductive article.

2. The device of claim 1, wherein the conductive article substantially conforms to said second surface.

3. The device of claim 1, further comprising a support structure for supporting the conductive article.

4. The device of claim 3, wherein the support structure includes a channel and wherein at least a portion of the conductive article is suspended over the channel.

5. The device of claim 1, wherein the conductive article is electromechanically responsive to electrical stimulation by the electrode.

6. The device of claim 1, wherein the non-woven fabric comprises substantially a monolayer of nanotubes.

7. The device of claim 1, wherein the flexible substrate comprises plastic.

* * * * *